(12) United States Patent
Song et al.

(10) Patent No.: US 9,943,624 B2
(45) Date of Patent: Apr. 17, 2018

(54) MULTI-FUNCTIONAL SURFACE COATING OF IMPLANTS

(71) Applicant: University of Massachusetts Medical School, Boston, MA (US)

(72) Inventors: Jie Song, Shrewsbury, MA (US); Pingsheng Liu, Worcester, MA (US); David C. Ayers, Southboroug, MA (US)

(73) Assignee: University of Massachusetts, Boston, MA (US)

( * ) Notice: Subject to any disclaimer, the term of this patent is extended or adjusted under 35 U.S.C. 154(b) by 185 days.

(21) Appl. No.: 14/646,723

(22) PCT Filed: Nov. 24, 2013

(86) PCT No.: PCT/US2013/071553
§ 371 (c)(1),
(2) Date: May 21, 2015

(87) PCT Pub. No.: WO2014/085275
PCT Pub. Date: Jun. 5, 2014

(65) Prior Publication Data
US 2015/0320913 A1  Nov. 12, 2015

Related U.S. Application Data

(60) Provisional application No. 61/732,239, filed on Nov. 30, 2012.

(51) Int. Cl.
C08F 122/10  (2006.01)
A61L 27/04  (2006.01)
(Continued)

(52) U.S. Cl.
CPC .............. *A61L 27/04* (2013.01); *A61L 27/06* (2013.01); *A61L 27/34* (2013.01); *A61L 27/54* (2013.01);
(Continued)

(58) Field of Classification Search
CPC .. C08D 133/08; C07K 9/008; A61L 2300/406
See application file for complete search history.

(56) References Cited

U.S. PATENT DOCUMENTS

| | | | | |
|---|---|---|---|---|
| 2009/0156460 | A1* | 6/2009 | Jiang | A61K 8/368 514/1.1 |
| 2010/0145286 | A1* | 6/2010 | Zhang | A61L 17/005 604/265 |
| 2011/0319569 | A1* | 12/2011 | Emrick | A61K 47/48176 525/326.6 |

* cited by examiner

Primary Examiner — Mark S Kaucher
(74) Attorney, Agent, or Firm — Milstein Zhang & Wu LLC

(57) ABSTRACT

The invention provides novel surface coatings having surface polymer brushes with zwitterionic and antibiotics-conjugated side chains and synergistic anti-fouling and bactericidal properties. The surface coatings may be prepared using highly efficient surface-initiated "living" polymerization. The design of the surface polymer brushes are highly modular, allowing independent tuning of the anti-fouling and bactericidal properties, e.g., by varying the chemical nature of the zwitterionic motif and the antibiotic agent, the chemistry through which the antibiotic agent is conjugated to the polymer side chains, the molecular weight of the polymer brushes (e.g., thickness of coating and density of respective functional motifs), and the spatial arrangement of the respective functional motifs (e.g., homopolymers, block copolymers, random copolymers) to achieve optimal and sustained anti-infection outcome for a given application.

8 Claims, 19 Drawing Sheets

(51) Int. Cl.
*A61L 27/06* (2006.01)
*C08F 222/10* (2006.01)
*A61L 27/34* (2006.01)
*A61L 29/16* (2006.01)
*A61L 31/16* (2006.01)
*A61L 27/54* (2006.01)
*A61L 29/02* (2006.01)
*A61L 29/08* (2006.01)
*A61L 31/02* (2006.01)
*A61L 31/10* (2006.01)
*C09D 133/08* (2006.01)
*C08F 293/00* (2006.01)
*C08F 220/38* (2006.01)

(52) U.S. Cl.
CPC .............. *A61L 29/02* (2013.01); *A61L 29/085* (2013.01); *A61L 29/16* (2013.01); *A61L 31/022* (2013.01); *A61L 31/10* (2013.01); *A61L 31/16* (2013.01); *C08F 122/10* (2013.01); *C08F 222/10* (2013.01); *C08F 293/005* (2013.01); *C09D 133/08* (2013.01); *A61L 2300/404* (2013.01); *A61L 2300/406* (2013.01); *A61L 2300/606* (2013.01); *A61L 2300/80* (2013.01); *C08F 2220/387* (2013.01)

A

B

C

D

A.

B.

C.

D.

E.

US 9,943,624 B2

MULTI-FUNCTIONAL SURFACE COATING OF IMPLANTS

PRIORITY CLAIMS AND RELATED PATENT APPLICATIONS

This application is the U.S. national phase of and claims priority to PCT/US13/71553, filed Nov. 24, 2013, which claims the benefit of priority from U.S. Provisional Application Ser. No. 61/732,239, filed on Nov. 30, 2012, the entire content of each of which is incorporated herein by reference in its entirety.

GOVERNMENT RIGHTS

The United States Government has certain rights to the invention pursuant to Grant No. R01AR055615 from the National Institutes of Health to the University of Massachusetts.

TECHNICAL FIELDS OF THE INVENTION

The invention generally relates to functional coatings. More particularly, the invention relates to multi-functional surface coatings of zwitterionic polymers for implants and other devices that have anti-fouling and bactericidal properties.

BACKGROUND OF THE INVENTION

Periprosthetic infection of metallic implants is one of the most serious complications in orthopedic surgery. (Lynch, et al. 2008 Annual Review of Medicine Vol. 59 415-428; Donlan 2001 Clinical Infectious Diseases 33, 1387-1392; Kurtz, et al. 2008 Journal of Arthroplasty 23, 984-991.) It occurs in 1% to 4% of primary arthroplasties and up to 30% of revision arthroplasties. Patients suffering from periprosthetic infections are often subjected to multiple surgical procedures with variable success rates, with some requiring devastating salvage procedures such as fusion, arthroplasty resection or even amputation. Although microbial contamination of implants can result from a number of causes including insufficient implant sterilization, contamination during the surgical manipulation, direct contact of infected tissue or remote site of infection, biofilm formation surrounding the implant is a common threat making serious local infections both more likely to occur and more difficult to eradicate.

Biofoulant adsorptions on a fouling implant surface provide a conditioning layer for microbial colonization and subsequent formation of biofilms. Bacteria embedded within biofilms can be 2-3 orders of magnitude harder to kill by most antibiotics and biocides, possibly through distinct mechanisms of antimicrobial actions. (Mah, et al. 2003 Nature 426, 306-310.) Treatment of biofilm-mediated infections of orthopedic implants often requires surgical replacement of the contaminated implants along with prolonged antibiotic therapy, which translate into longer hospitalization, higher medical costs, severe functional impairment, morbidity, and increased mortality for patients.

To prevent such devastating events, implant surface modifications aimed at reducing biofouling and attenuating subsequent adverse inflammatory responses and risks for infections have long been sought after. Experiments and theoretic modeling carried out with well-controlled model systems, such as hydrophilic poly(ethylene glycol) (PEG) or zwitterionic self-assembled monolayers formed on atomically flat metal substrates, have elucidated multiple chemical and physical parameters governing the efficiency of anti-fouling including the correlation of the dynamics and structure of interfacial water with non-fouling properties. (Chen, et al. 2010 Polymer 51, 5283-5293.) Clinical translation of these basic findings, however, has been hampered by the topological and compositional complexity of commercial metallic implant surfaces and the sophisticated dynamic tissue environment that cannot be simulated by simple model systems.

Thus, an un-met need continues to exist for viable surface modification strategies that simultaneously and adequately address the anti-fouling and bactericidal needs.

SUMMARY OF THE INVENTION

The invention provides novel surface coatings having surface polymer brushes with zwitterionic and antibiotic-conjugated side chains and synergistic anti-fouling and bactericidal properties. The surface coatings may be prepared using highly efficient surface-initiated "living" polymerization. The design of the surface polymer brushes are highly modular, allowing independent tuning of the anti-fouling and bactericidal properties (e.g., by varying the chemical nature of the zwitterionic motif and the antibiotic agent), the chemistry through which the antibiotic agent is conjugated to the polymer side chains, the molecular weight of the polymer brushes (e.g., thickness of coating and density of respective functional motifs), and the spatial arrangement of the respective functional motifs (e.g., homopolymers, block copolymers, random copolymers) to achieve optimal and sustained anti-infection outcome for a given application.

The coating strategy disclosed herein can be broadly applied to a variety of implants and devices, such as metallic and synthetic implants, screws, fixators and surgical devices without affecting their structural and mechanical integrity, facilitating subsequent clinical translation of this technology to benefit both military and civilian populations.

In one aspect, the invention generally relates to an anti-fouling and bactericidal composition comprising a zwitterionic polymer comprising antibacterial moieties. The zwitterionic polymer may be any suitable polymer grafted with zwitterionic groups. The polymer may be a homopolymer or a copolymer (e.g., a random copolymer or a block copolymer). The zwitterionic groups used to graft the polymer may be any suitable zwitterionic groups such as phosphorylcholine, sulfobetaine, and carboxybetaine.

In another aspect, the invention generally relates to an anti-fouling and bactericidal surface of a solid substrate. The surface has a layer of polymer brushes comprising anti-fouling zwitterionic polymers and/or antibacterial polymer conjugates. The surface may be a surface of any suitable substrate, metallic or non-metallic, synthetic or non-synthetic. In certain preferred embodiments, the solid substrate is a medical implant or a component thereof, such as a catheter, a vascular stent, a dental implant, an orthopedic implant.

In yet another aspect, the invention generally relates to an implant substrate having a surface covalently bonded thereto a layer of a co-polymer comprising repeating units having structures of:

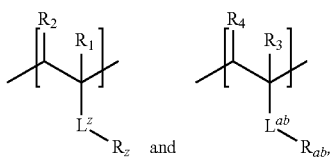

wherein
R$_1$, R$_3$ each is independently a hydrogen, alkyl, alkyloxy;
R$_2$, R$_4$ each is independently a hydrogen, (C$_1$-C$_{15}$) alkyl, (C$_1$-C$_{15}$) alkyloxy;
L$^z$ is a linking group;
L$^{ab}$ is a linking group;
R$_z$ is a pendant group comprising a zwitterionic group; and
R$_{ab}$ is a pendant group comprising an antibacterial moiety.

In certain preferred embodiments, the co-polymer comprises the structure:

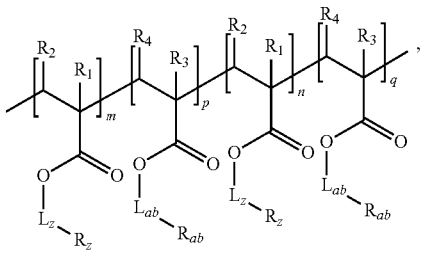

wherein each of m, n, p, and q is an integer selected from about 0 to about 500.

In yet another aspect, the invention generally relates to a co-polymer comprising repeating units having structures of:

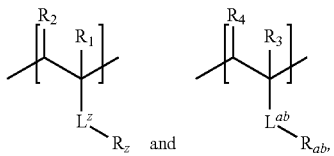

wherein
R$_1$, R$_3$ each is independently a hydrogen, alkyl, alkyloxy;
R$_2$, R$_4$ each is independently a hydrogen, (C$_1$-C$_{15}$) alkyl, (C$_1$-C$_{15}$) alkyloxy;
L$^z$ is a linking group;
L$^{ab}$ is a linking group;
R$_z$ is a pendant group comprising a zwitterionic group; and
R$_{ab}$ is a pendant group comprising an antibacterial moiety.

In certain preferred embodiments, the co-polymer has the structure:

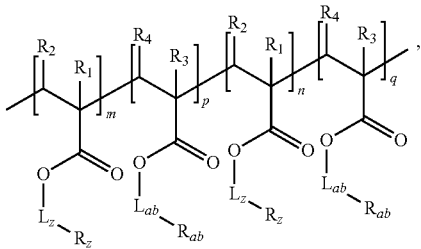

wherein each of m, n, p, and q is an integer selected from about 0 to about 500.

DESCRIPTION OF THE INVENTION

Figure 1:
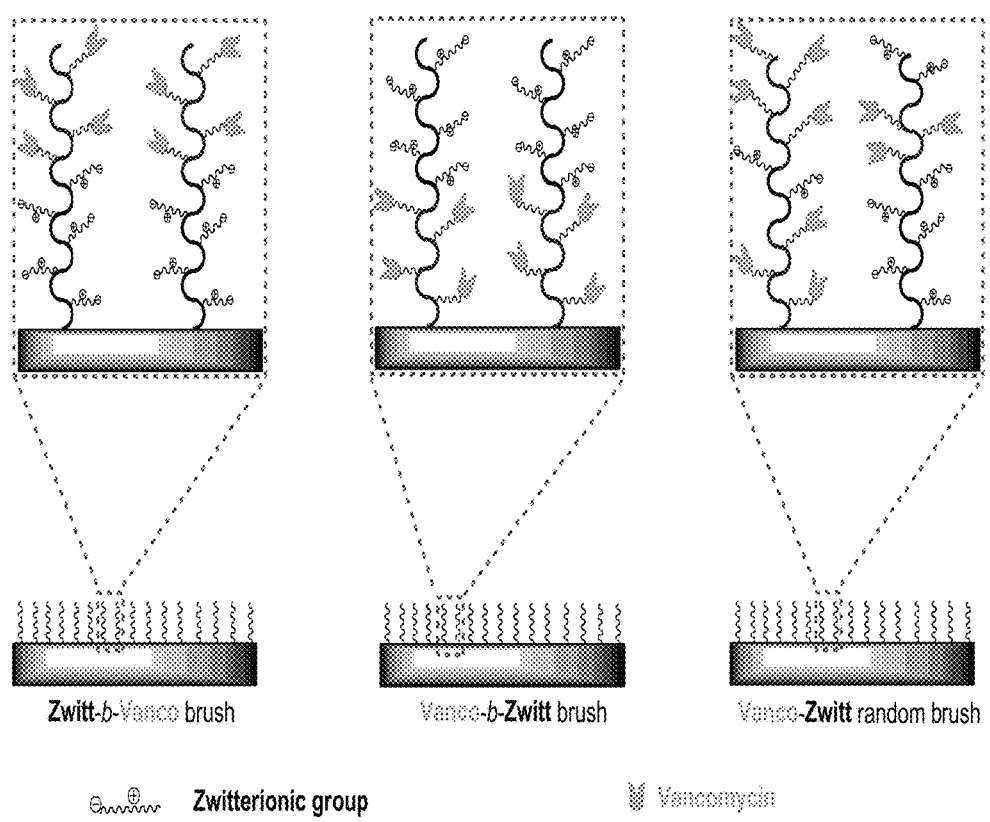
FIG. 1. Schematic illustration of block-copolymer brushes designed as anti-fouling and bactericidal surface coatings for titanium and titanium alloy implants.

This invention provides a novel, multi-functional implant surface coating designs with tunable anti-fouling and bactericidal properties for minimized biofilm formation and infection. The implant surface covalently immobilized with biocompatible functional block polymer brushes composing conjugated blocks of zwitterionic and bactericidal.

To achieve optimal anti-fouling effect of commercial metallic implants, polymer brushes with tightly controlled yet tunable molecular weights (thickness of coating) and low-fouling side chain chemistries are preferably covalently grafted from the implant surface. The lack of reliable/robust strategies for anchoring small molecule initiators to the surface oxide, tendency for PEG-based surface coatings to auto-oxidize in physiological environment thereby losing the anti-fouling properties over time, and less-than-optimal control over the kinetics of surface-initiated polymerization of low fouling zwitterionic polymer brushes (e.g., broad molecular weight distributions) are major bottleneck issues to overcome. (Hucknall, et al. 2009 *Advanced Materials* 21, 2441-2446; Herold, et al. 1989 *Biochemical Pharmacology* 38, 73-76; Wang, et al. 2003 *European Polymer Journal* 39, 2107-2114; Liaw, et al. 1993 *Polymer International* 30, 381-386.)

As no anti-fouling surfaces are free from surface defects, fouling-mediated risk for bacterial adhesion and infection still necessitates the design of surface coatings that are also bactericidal. Most common practice in affording implants with bactericidal properties is by non-covalently encapsulating and release antibiotics near the implant. (Li, et al. 2010 *J of Controlled Release* 145, 221-230; Hanssen, et al. 2004 *Clin Orthop Relat Res* 427, 79-85.) Such a local delivery strategy, however, often suffers from sub-optimal drug release kinetics and associated side effects (e.g. burst release could lead to significant systemic toxicity and the quick depletion of local drug concentration while too slow of a release comprises short-term bactericidal efficiency). (Anderson, et al. 2009 *Biomaterials* 30, 5675-5681; Penner, et al. 1996 *J of arthroplasty* 11, 939-944.) An alternative strategy recently being pursued is to covalently tether antibiotics on the implant surface, which typically involves binding small molecule linkers to surface metal oxides followed by conjugation of the drug using conventional esterification/amidation chemistry. (Antoci, et al. 2008 *Biomaterials* 29, 4684-4690; Antoci, et al. 2007 *Clinical Orthopaedics and Related Research*, 81-87; Edupuganti, et al. 2007 *Bioorganic & Medicinal Chemistry Letters* 17, 2692-2696; Jose, et al. 2005 *Chemistry & Biology* 12, 1041-1048; Antoci, et al. 2007 *Journal of Orthopaedic Research* 25, 858-866.) Such an approach limits the achievable surface density of antibiotics to the available surface oxide sites. In addition, such surface coatings do not prevent the attachment of killed bacteria or the built up of biofilms since they are not anti-fouling in nature. Indeed, although implants covalently modified with vancomycin using such a strategy indeed reduced infections in vivo in the short term (for a couple of weeks), it failed to completely inhibit the infection in the long term. (Antoci, et al. 2007 *Clinical Orthopaedics and Related Research*, 88-95.) Such sub-optimal densities of covalently linked antibiotics may in fact raise the risk for developing drug resistance.

A parallel approach in addressing periprosthetic infections is the local delivery of antibiotics, by either non-covalent encapsulation/release of the drug near implant surface or by covalent tethering of the drug on the implant. Non-covalent local delivery of antibiotics often suffers from sub-optimal drug release kinetics and associated side effects (e.g. burst release could lead to significant systemic toxicity and quick depletion of local drug concentration, while too slow of a release comprises short-term bactericidal efficiency and increases long-term risk for developing drug resistance). Existing covalent attachment of antibiotics on metal surfaces involves binding small molecule linkers to surface metal oxides followed by conjugation of the drug using conventional esterification/amidation chemistry. Such an approach limits the achievable surface density of antibiotics to the available surface oxide sites and the yield of the coupling chemistry. In vivo evaluations of implants modified with vancomycin using such a strategy revealed improved anti-bacterial properties in the short term supporting the retention of bioactivity of vancomycin upon covalent modification, but also the failure to completely inhibit the infection in the longer term, highlighting limitations of this approach. (Antoci, et al. 2007 *Clin. Orthop. Relat. Res.* 88-95.) Such sub-optimal densities of covalently linked antibiotics also raise the risk for developing drug resistance.

The challenges associated with anti-fouling and antibacterial surface coatings are addressed by employing significantly improved surface-initiated polymerization of low-fouling, zwitterionic polymer brushes and higher-density covalent presentation of antibiotics (e.g., vancomycin). The general coating strategy applies to a wide range of implants.

The block polymer brushes are fabricated through surface-initiated atom transfer polymerization, making the brushes well controllable and tunable in molecule weight, chain length, as well as the coating thickness on the surface of the implant. This feature is critical in achieving optimal balance of anti-fouling and bactericidal properties to reduce infections.

The vancomycin is conjugated to the brush through "click" reaction, providing a highly efficient fabrication of a dense antimicrobial surface. The density of the vancomycin in the polymer coating is highly tunable by facile control of the molecule weight (repeat unit) of the polymer block. Much denser vancomycin can be achieved by this approach comparing to the direct immobilization of vancomycin monolayer to metal surface (Antoci, et al. 2007 *Clin. Orthop. Relat. Res.* 88-95), making it far more potent in its bactericidal properties.

These strategies are implemented, as illustrated in FIG. 1, in a synergistic fashion to achieve synergistic anti-fouling and bactericidal properties of the surface coating, thereby optimizing the anti-infection outcome. Technically, highly controlled surface initiated polymerization technique (SI-ATRP) and high fidelity "click" chemistry were chosen to realize this goal.

Figure 2:
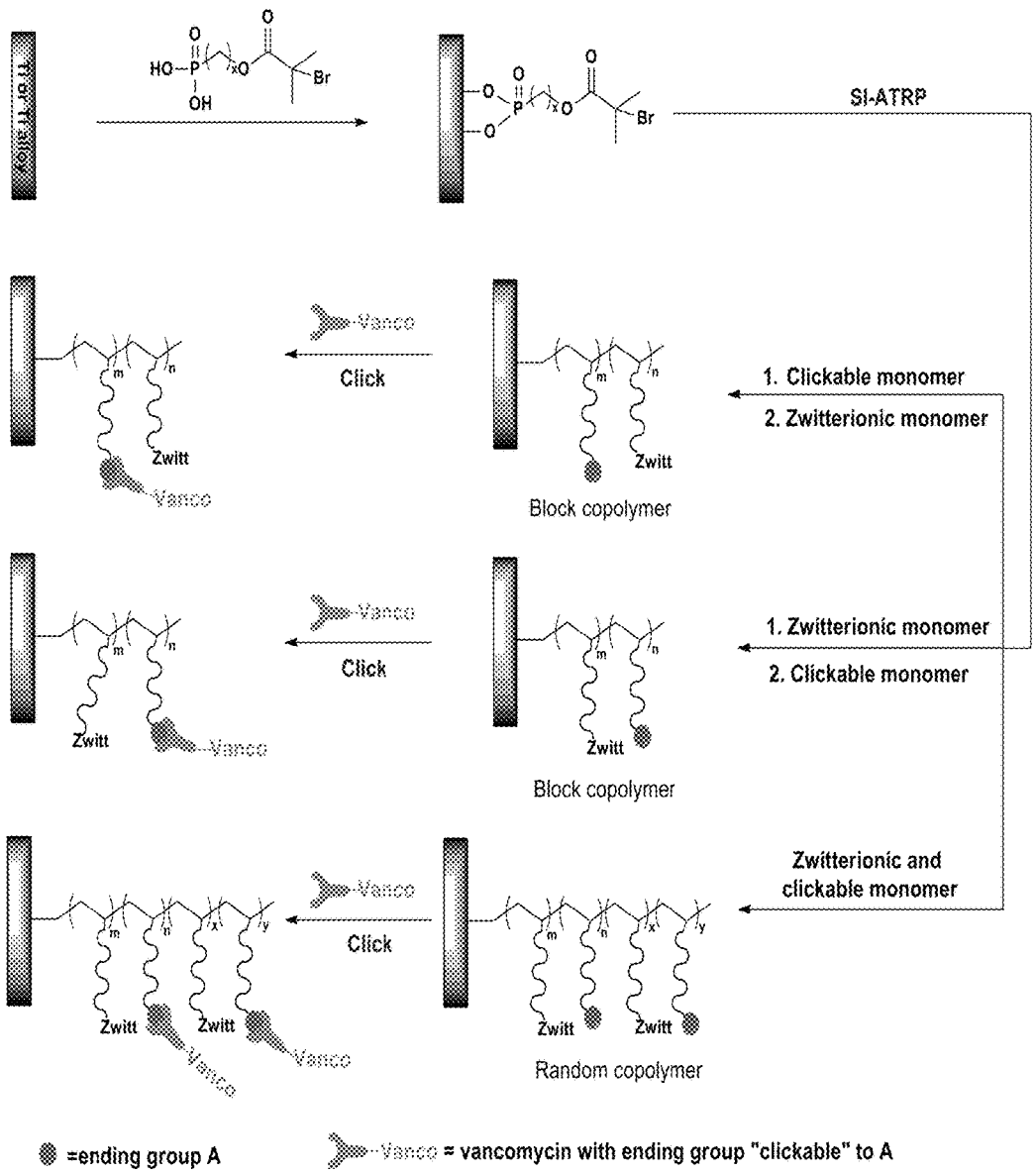
FIG. 2. Representative synthetic schemes of the step-wise surface modification strategies.

To graft anti-fouling/bactericidal polymers to metallic implants, surface-initiated atom transfer radical polymerization (SI-ATRP) was chosen to precisely control polymer chain length (molecular weight/MW), polydispersity index (PDI), side chain functional group density and blockiness of the surface polymer brushes (e.g., block vs. random copolymers). A robust protocol was developed for attaching small molecule phosphonic acid-based linkers with bromide terminals to Ti6Al4V alloy surfaces as surface-bound initiators for SI-ATRP (FIG. 2).

Figure 3:
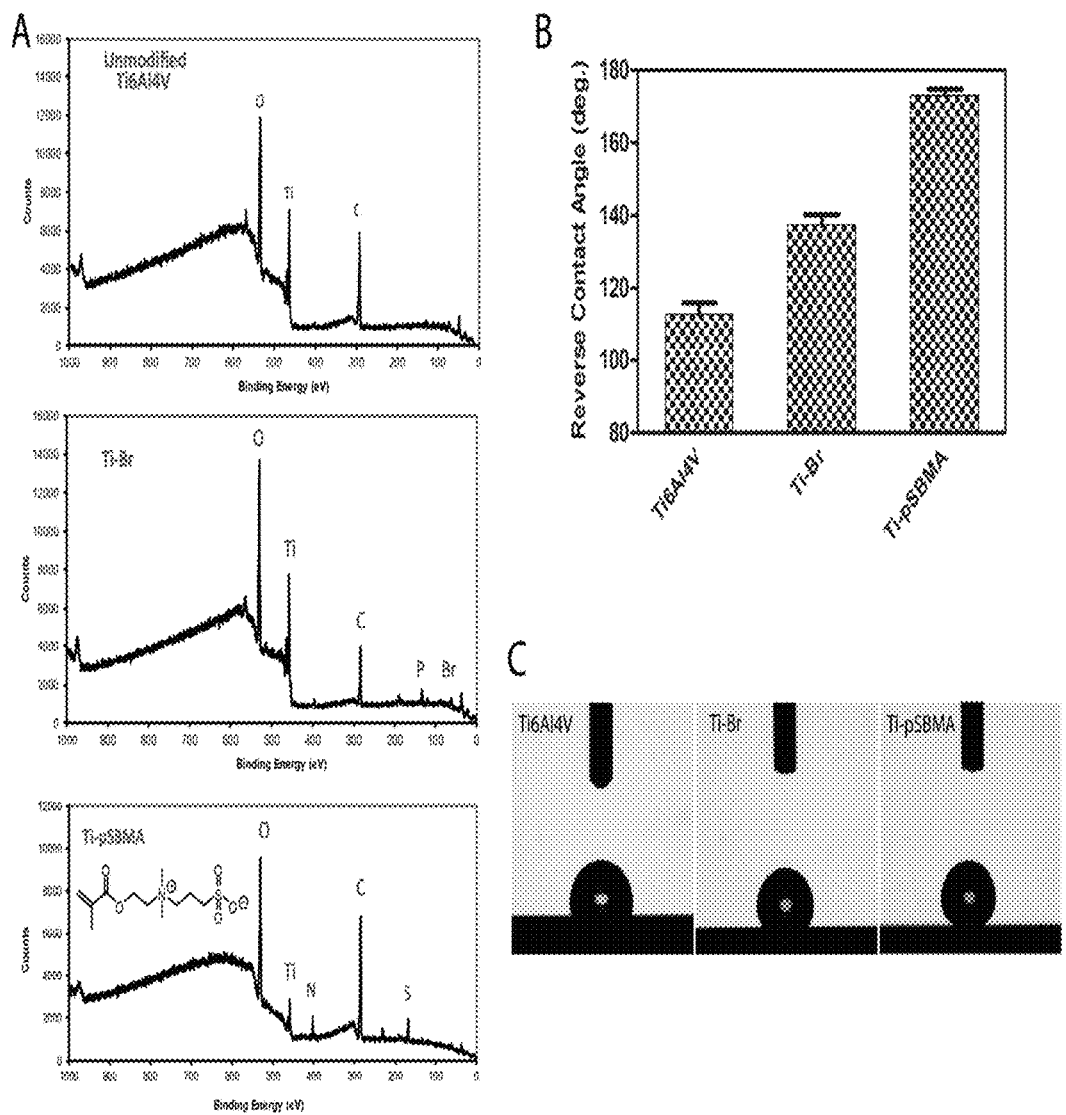
FIG. 3. XPS (A) and contact angle (B & C) changes confirming the attachment of Br-terminated ATRP-initiatiors on Ti6Al4V surfaces, and subsequent grafting of zwitterionic brushes polymerized from SBMA.

The consistency of the surface attachment of the small molecule linker and subsequent conversion to SI-ATRP initiators were validated by the change in surface wettability (contact angle) and surface chemical composition (X-ray photoelectron spectroscopy), as shown in FIG. 3. The resulting surface-bound ATRP initiators (2, FIG. 2) were stable enough to withstand sustained sonication/heating in various solvents, making it uniquely suited for the proposed surface modifications by SI-ATRP.

Figure 4:
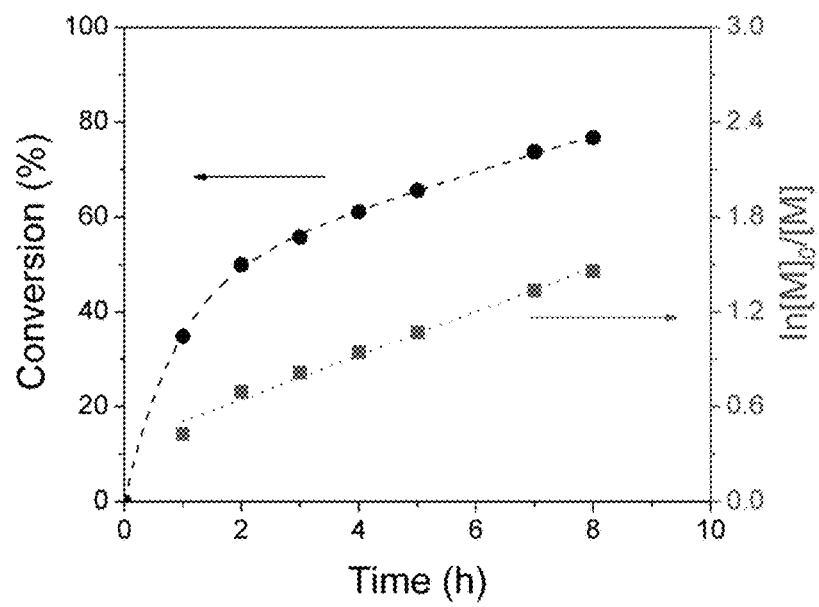
FIG. 4. Well controlled ATRP of zwitterionic monomer SBMA carried out in an ionic liquid at room temperature (A & B) and at 60° C. (C) revealed outstanding control over the MW, polydispersity index (M$_w$/M$_n$, PDI), and temperature dependent polymerization kinetics (C).
Figure 4:
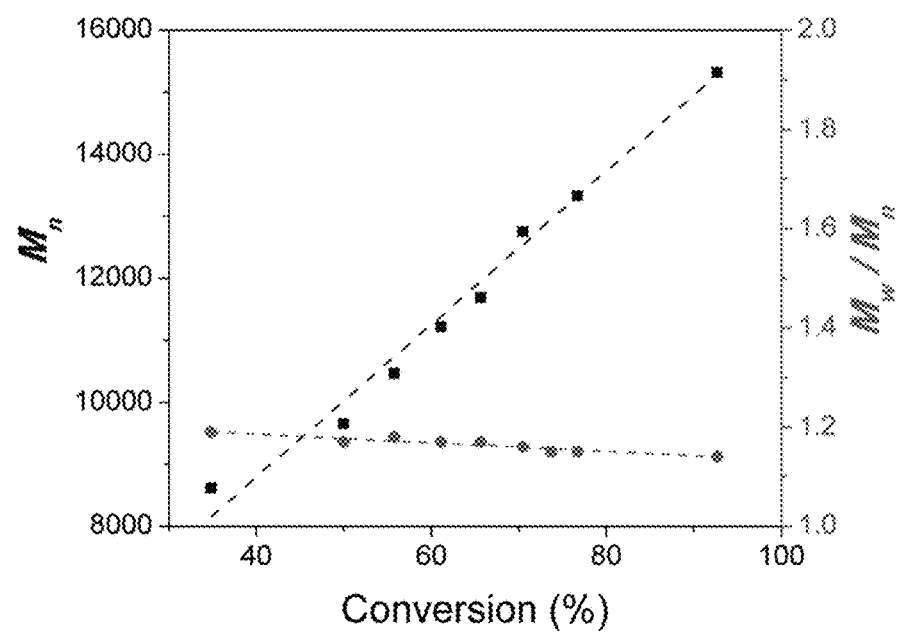
Figure 4:
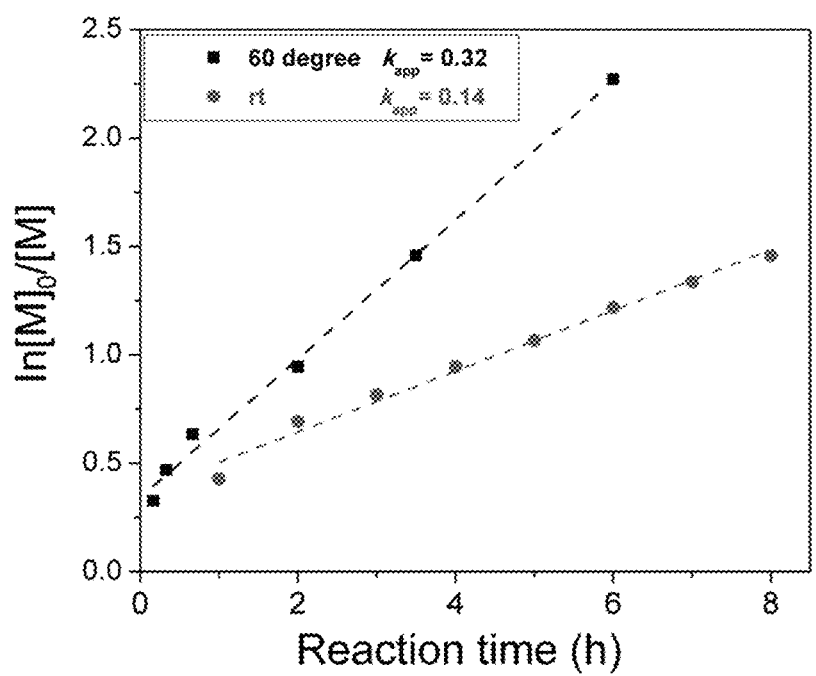

Effective anti-fouling coatings were screened by grafting zwitterionic polymer brushes with varying thicknesses (MW), side chain chemistries (MPC, SB vs. CB, FIG. 2) and packing densities. Using ionic liquid as optimized solvent, zwittionic polymers were prepared by ATRP with significantly improved control over polymerization kinetics, conversion, MW and extremely narrow PDI ($M_w/M_n \sim 1.1$) as shown in FIG. 4. This addresses a major challenge in controlled synthesis of zwitterionic polymers.

In one aspect, the invention generally relates to an anti-fouling and bactericidal composition comprising a zwitterionic polymer comprising antibacterial moieties.

The zwitterionic polymer may be any suitable polymer grafted with zwitterionic groups. The polymer may be a homopolymer or a copolymer (e.g., a random copolymer or a block copolymer). The zwitterionic groups used to graft the polymer may be any suitable zwitterionic groups such as phosphorylcholine, sulfobetaine, and carboxybetaine.

Phosphorylcholine has the structure of

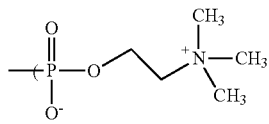

The sulfobetaine has the structure:

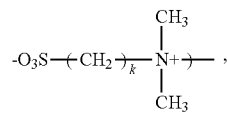

wherein k is an integer from about 1 to about 15.

Carboxybetaine has the structure:

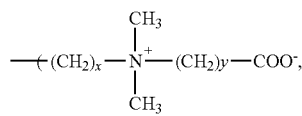

wherein y is an integer from about 1 to about 15.

In certain preferred embodiments, the polymers comprise both zwitterionic side chains and side chains with covalently linked antibacterial moieties. Any suitable antibacterial moieties may be used such as those selected from beta-lactam antibiotics, tetracyclines, aminoglycosides, macrolides, chloramphenicol, ivermectin and rifamycins.

In some embodiments, the zwitterionic polymer has a molecular weight from about 1,000 Da to about 300,000 Da (e.g., from about 2,000 Da to about 300,000 Da, from about 5,000 Da to about 300,000 Da, from about 10,000 Da to about 300,000 Da, from about 20,000 Da to about 300,000 Da, from about 50,000 Da to about 300,000 Da, from about 75,000 Da to about 300,000 Da, from about 100,000 Da to about 300,000 Da, from about 150,000 Da to about 300,000 Da, from about 200,000 Da to about 300,000 Da, from about 1,000 Da to about 250,000, from about 1,000 Da to about 200,000, from about 1,000 Da to about 150,000 from about 1,000 Da to about 125,000 Da, from about 100,000 Da to about 75,000 Da, from about 1,000 Da to about 50,000 Da, from about 1,000 Da to about 25,000 Da, from about 1,000 Da to about 10,000 Da, from about 5,000 Da to about 300,000 Da, from about 5,000 Da to about 250,000 Da, from about 10,000 Da to about 250,000 Da, from about 10,000 Da to about 200,000 Da, from about 10,000 Da to about 150,000 Da, from about 10,000 Da to about 100,000 Da, from about 10,000 Da to about 50,000 Da).

In another aspect, the invention generally relates to an anti-fouling and bactericidal surface of a solid substrate. The surface has a layer of a zwitterionic polymer comprising antibacterial moieties.

The surface may be a surface of any suitable substrate, metallic or non-metallic, synthetic or non-synthetic. In certain embodiments, the solid substrate is a metallic substrate (e.g., stainless steel, titanium, cobalt, chromium, tantalum, magnesium, and/or nickel, or an alloy thereof). In certain embodiments, the solid substrate is a synthetic polymeric substrate (e.g., UHMWPE, crosslinked UHMWPE, polyurethanes, PEEK, polylactides, polyesters).

In certain preferred embodiments, the solid substrate is a medical implant or a component thereof, such as a catheter, a vascular stent, a dental implant, an orthopedic implant.

Exemplary bone, joint, and dental metallic implants include: fixation plates, IM rods, screws, total joint replacement prosthetics; dental filler/composites; spine fusion metallic cages. Exemplary orthopedic implants include: an implant for total knee replacement (TKR), total hip replacement (THR), total shoulder replacement (TSR), total elbow replacement (TER), total wrist replacement (TWR), total ankle replacement (TAR), or a component thereof.

The zwitterionic polymer may be covalently linked to the surface of the substrate or non-covalently coated to the surface of the substrate.

The zwitterionic groups used to graft the polymer may be any suitable zwitterionic groups such as phosphorylcholine, sulfobetaine, and carboxybetaine.

In certain preferred embodiments, the surface grafted polymers comprise both zwitterionic side chains and side chains with covalently linked antibacterial moieties. Any suitable antibacterial moieties may be used such as those selected from beta-lactam antibiotics, tetracyclines, aminoglycosides, macrolides, chloramphenicol, ivermectin and rifamycins.

In yet another aspect, the invention generally relates to an implant substrate having a surface covalently bonded thereto a layer of a co-polymer comprising repeating units having structures of:

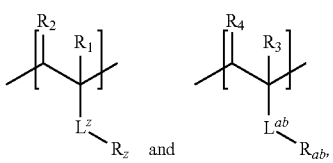

wherein
$R_1$, $R_3$ each is independently a hydrogen, alkyl, alkyloxy;
$R_2$, $R_4$ each is independently a hydrogen, ($C_1$-$C_{15}$) alkyl, ($C_1$-$C_{15}$) alkyloxy;
$L^z$ is a linking group;
$L^{ab}$ is a linking group;
$R_z$ is a pendant group comprising a zwitterionic group; and
$R_{ab}$ is a pendant group comprising an antibacterial moiety.

In certain preferred embodiments, the co-polymer comprises the structure:

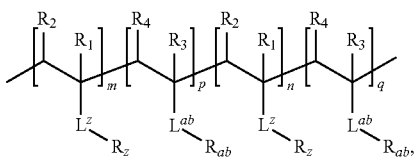

wherein each of m, n, p, and q is an integer selected from about 0 to about 500 (e.g., about 50, 100, 150, 200, 250, 300, 350, 400, 450, 500).

In certain preferred embodiments, the co-polymer comprises repeating units of structures:

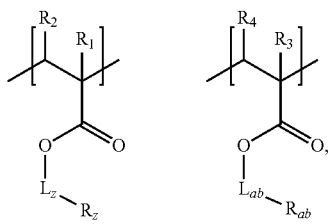

wherein
$L_z$ is a linking group; and
$L_{ab}$ is a linking group.

In certain preferred embodiments, the co-polymer comprises the structure:

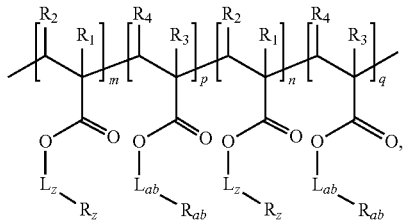

wherein each of m, n, p, and q is an integer selected from about 0 to about 500 (e.g., about 50, 100, 150, 200, 250, 300, 350, 400, 450, 500).

In certain preferred embodiments, each of $R_1$, $R_3$, $R_2$, and $R_4$ is hydrogen, each of $L_z$ and $L_{ab}$ is independently —$(CH_2)_i$—, wherein i is an integer from about 1 to about 20 (e.g., 1, 2, 3, 4, 4, 6, 10, 12, 15, 18, 20). In certain preferred embodiments, at least one of $R_1$, $R_3$, $R_2$, and $R_4$ is not hydrogen.

In yet another aspect, the invention generally relates to a co-polymer comprising repeating units having structures of:

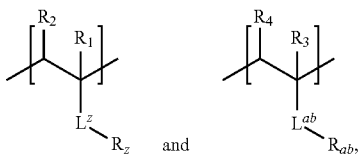

wherein
$R_1$, $R_3$ each is independently a hydrogen, alkyl, alkyloxy;
$R_2$, $R_4$ each is independently a hydrogen, ($C_1$-$C_{15}$) alkyl, ($C_1$-$C_{15}$) alkyloxy;
$L^z$ is a linking group;
$L^{ab}$ is a linking group;
$R_z$ is a pendant group comprising a zwitterionic group; and
$R_{ab}$ is a pendant group comprising an antibacterial moiety.

In certain preferred embodiments, the co-polymer has the structure:

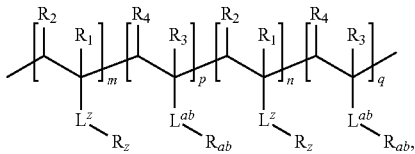

wherein each of m, n, p, and q is an integer selected from about 0 to about 500 (e.g., about 50, 100, 150, 200, 250, 300, 350, 400, 450, 500).

In certain preferred embodiments, the co-polymer comprises repeating units of structures:

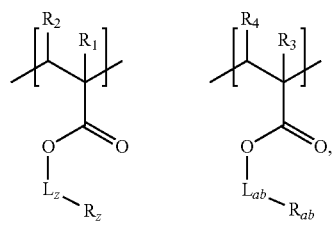

wherein
$L_z$ is a linking group; and
$L_{ab}$ is a linking group.

In certain preferred embodiments, the co-polymer has the structure:

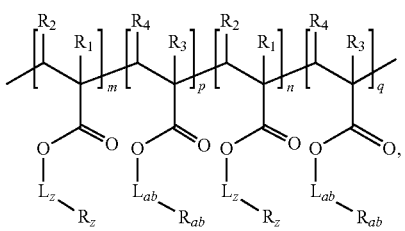

wherein each of m, n, p, and q is an integer selected from about 0 to about 500 (e.g., about 50, 100, 150, 200, 250, 300, 350, 400, 450, 500).

In certain preferred embodiments, the antibacterial moiety is vancomycin or a derivative thereof.

EXAMPLES

Preparation of Well-Controlled Zwitterionic Polymers pSBMA by ATRP in Ionic Liquid Traditional radical polymerizations of zwitterionic vinyl monomers containing sulfobetaine, carboxybetaine, and phosphobetaine groups typically resulted in polymers with broad molecular weight distributions (PDI or $M_w/M_n>1.5$). (Wang, et al. 2003 *European Polymer Journal* 39, 2107-2114; Liaw, et al. 1993 *Polymer International* 30, 381-386.) Even using controlled living polymerization processes such as atom transfer radical polymerization (ATRP), zwitterionic polymers with narrow polydispersity (PDI<1.2) have been difficult to obtain because of the unique ionic strengths and solubility behavior of zwitterioic monomers and polymers in common reaction media. For instance, zwitterionic monomers and polymers are insoluble in nonpolar organic solvents and are only soluble in limited protic solvents such as aqueous solutions but tend to self-aggregate as driven by their low ionic strengths and strong attractive electrostatic interactions in water. Fluoroalcohol and ionic liquids have recently been shown effective in screening such strong interactions between zwitterionic groups, thereby improving the solubility of both the monomers and polymers and enabling well-controlled polymerization of zwitterionic monomers by ATRP. (Terayama, et al. 2011 *Macromolecules* 44, 104-111.)

Figure 5:
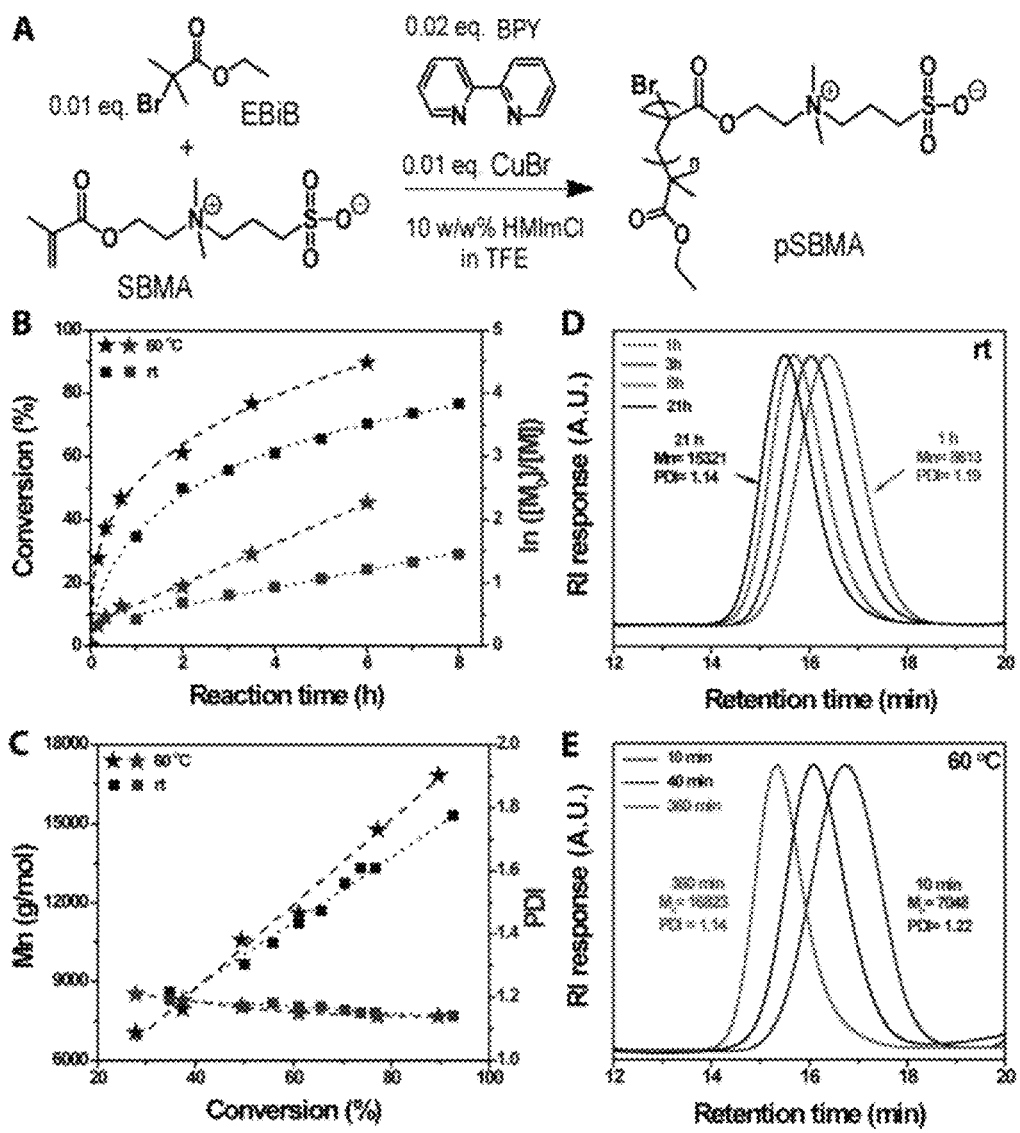
FIG. 5. (A) Synthetic scheme of ATRP of zwitterionic monomer SBMA carried out in 10 w/w % HMImCl in TFE at room temperature (rt) or 60° C. [SBMA]=1 M; [SBMA]:[EBiB]:[CuBr]:[BPY]=100:1:1:2. (B) Monomer conversion (%) and monomer conversion index ln([M]$_0$/[M]) as a function of reaction time at room temperature ("rt") (squares) and 60° C. (stars); (C) Molecular weight and PDI as a function of monomer conversion (%) at rt (squares) and 60° C. (stars); (D) GPC traces monitoring the reaction at rt; (E) GPC traces monitoring the reaction at 60° C. Detailed GPC conditions are described in B2.5.

Using 10 w/v % 1-hexyl-3-methylimidazolium chloride (HMImCl) in (2,2,2-trifluoroethanol (TFE) as a solvent and ethyl α-bromoisobutyrate (EBiB) as an initiator (FIG. 5A), pSBMA was successfully prepared by ATRP with high monomer conversions and low PDI. Briefly, 2,2'-bipyridine (BPY) was dissolved in TFE in a Schlenk flask and degassed by three "freeze-pump-thaw" cycles to remove oxygen. The flask was then back-filled with argon and CuBr was added. The mixture was stirred for 10 min to ensure the formation of the copper catalyst complex. Monomer SBMA (1 M; targeting DP=100), initiator ethyl α-bromoisobutyrate (EBiB) and HMImCl were then dissolved in TFE under stirring at room temperature in another Schlenk flask to achieve a [SBMA]:[EBiB]:[CuBr]:[BPY] ratio of 100:1:1:2 and an ionic liquid concentration of 10 w/w % HMImCl in TFE. The flask was degassed by three "freeze-pump-thaw" cycles before the copper catalyst complex was added by syringe. Polymerization was carried out at either room temperature or 60° C. An aliquot of the reaction mixture was retrieved for $^1$H NMR and GPC monitoring at various time points. The reactor was exposed to air to terminate the polymerization after 6-8 h. The polymerization solution was precipitated in methanol to obtain the pSBMA polymer. Using this process, 90% monomer conversion was achieved with a molecular weight of ~17 KDa in 6 h at 60° C., with extremely low PDI of ~1.15 (FIGS. 5B, 5C, & 5E). By altering the ratio of monomer and initiators, pSBMA with varying degree of polymerizations (DP=50, 100, or 200) were prepared with monomer conversion as high as 97-99% when the polymerization time was extended to 18 h at 60° C. A linear relationship between the monomer conversion index $\ln([M]_0/[M])$ and reaction time at both room temperature and 60° C. revealed a first-order polymerization kinetics (FIG. 5B, blue), with the rate of monomer conversion positively correlated with the reaction temperatures (FIGS. 5B-5D). The higher temperature reaction led to slightly higher molecular weight polymers than the room temperature reactions, with equally narrow PDI (FIGS. 5C & 5E). The high affinities of TFE and HMImCl for SBMA and pSBMA have likely ensured a homogeneous polymerization media, resulting in tightly controlled ATRP.

Grafting Well-Controlled Zwitterionic Polymer or Block Copolymer Surface Brushes from Ti6Al4V by SI-ATRP The 6-h ATRP at 60° C. using 10 w/v % HMImCl in TFE as a solvent, a condition identified above as optimal for preparing pSBMA in solution, was applied to graft zwitterionic pSBMA and amphiphilic block copolymer surface brushes from Ti6Al4V using SI-ATRP.

A2.1. Ti6Al4V alloy substrate preparation: Ti6Al4V plate (1.3 mm thick, Titanium Metal Supply Inc.) was cut into 10×10-mm² squares, sequentially polished under water with 600-, 1500-, and 3000-grit silicon carbide sandpapers, and ultrasonically cleaned with hexane (10 min), dichloromethane (10 min), and acetone (10 min) sequentially. The substrates were then annealed at 120° C. in an oven and cleaned by air plasma for 2 min in a Harrick PDC-001 plasma chamber (Harrick Plasma, Ithaca, N.Y.).

Preparation of Initiator (2-Bromo-2-Methylpropanoyloxy) Methylphosphonic Acid (PA-O—Br)

A number of small molecule anchors have been used for attaching polymer brushes to metallic surfaces, including 3,4-dihydroxyphenylalanine (a mussel adhesive protein component), anachelin (a cyanobacterial iron chelator), and aminopropylated silane linker. (Dalsin, et al. 2003 *Journal of the American Chemical Society* 125, 4253-4258; Dalsin, et al. 2005 *Langmuir* 21, 640-646; Fan, et al. 2005 *Journal of the American Chemical Society* 127, 15843-15847; Wach, et al. 2008 *Chemistry-a European Journal* 14, 10579-10584; Zurcher, et al. 2006 *Journal of the American Chemical Society* 128, 1064-1065; Wach, et al. 2008 *Angewandte Chemie-International Edition* 47, 7123-7126; Antoci, et al. 2008 *Biomaterials* 29, 4684-4690; Antoci, et al. 2007 *Clinical Orthopaedics and Related Research*, 81-87; Edupuganti, et al. 2007 *Bioorganic & Medicinal Chemistry Letters* 17, 2692-2696; Jose, et al. 2005 *Chemistry & Biology* 12, 1041-1048.) Here phosphonic acid-based small molecule anchor was chosen due to its strong binding affinity to the surface metal oxides of Ti6Al4V and the ease of its functionalization to introduce a terminal bromide to enable SI-ATRP.

Figure 6:
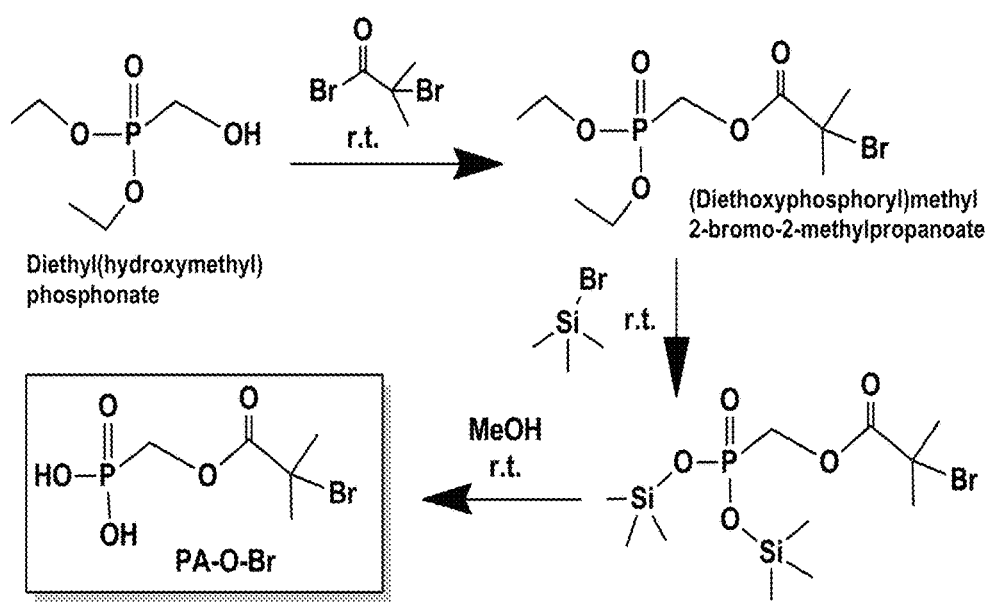
FIG. 6. Synthetic scheme for the preparation of initiator PA-O—Br.

(Diethoxyphosphoryl)methyl 2-bromo-2-methylpropanoate (1.06 g, 3.34 mmol), prepared from diethyl (hydroxymethyl)phosphonate and purified following literature procedures in 64% yield, was dissolved in 20-mL anhydrous dichloromethane in a dry flask before bromotrimethylsilane (1.86 g, 12 mmol) was injected. (Kim, et al. 2010 *Langmuir* 26, 2083-2092.) The reaction was allowed to proceed under argon at room temperature overnight (FIG. 6). After removing the solvent under vacuum, anhydrous methanol (15 mL) was added to the product and stirred at overnight. Yellowish oil obtained after removing solvent was further purified by recrystallization in dichloromethane, yielding white crystals of the initiator PA-O—Br in 47% yield. $^1$H NMR (400 MHz, methanol-$d_4$): δ 4.40-4.38 (d, 2H), 1.94 (s, 6H) ppm; $^{13}$C NMR (100 MHz, methanol-$d_4$): δ 171.1, 60.1, 58.5, 55.2, 29.9 ppm; $^{31}$P NMR (170 MHz, methanol-$d_4$): δ 14.9 ppm. MS (ESI, m/z): $C_5H_{10}BrO_5P$ [M+H]$^+$, calculated 261.09. found 261.01.

Surface Immobilization of Initiator PA-O—Br on Ti6Al4V Substrates

Annealed and plasma-cleaned Ti6Al4V substrates (40 pieces) were placed in 40 mL of 3-mM anhydrous methane solution of PA-O—Br under dark at room temperature for 24 h, allowing the phosphonic acid group to attach to the thin oxide layer of the Ti6Al4V surface. The substrates were then retrieved from the PA-O—Br solution and annealed at 110° C. for 15 min, followed by extensive sonication in methane (10 min at a time, twice). The Br-immobilized substrates were then dried under vacuum and immediately used for subsequent SI-ATRP.

Figure 7:
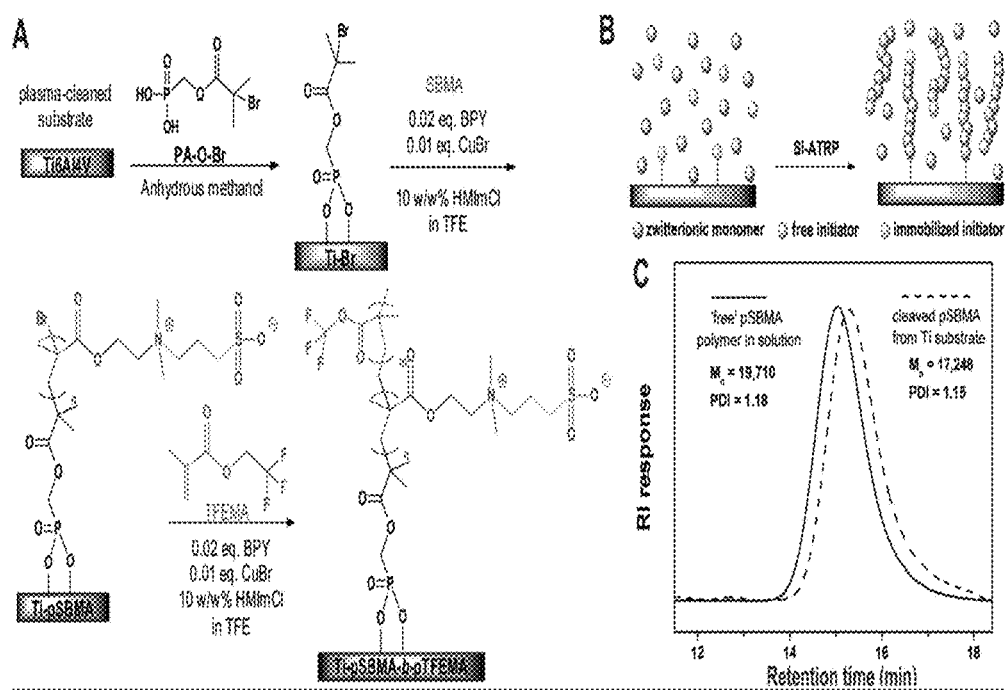
FIG. 7. (A) Synthetic scheme for grafting pSBMA or pSBMA-b-pTFEMA block copolymer brushes from the surface of plasma-cleaned Ti6Al4V substrates using SI-ATRP; (B) Cartoon depiction of grafting zwitterionic polymer brushes on a Ti substrate via SI-ATRP with simultaneous solution polymerization to form "free" zwitterionic polymer via ATRP; (C) GPC traces showing that pSBMA cleaved off from the Ti substrate following SI-ATRP exhibit similar molecular weights and low PDI as the "free" pSBMA formed in the solution. Detailed GPC conditions are described in B2.5.

Grafting of pSBMA Polymer Brushes or pSBMA-b-pTFEMA Block Polymer Brushes from Br-Immobilized Ti6Al4V Substrates by SI-ATRP The grafting of zwitterionic polymer brushes or block copolymer brushes via SI-ASRP is schematically illustrated in FIG. 7A. The preparation of the copper catalyst complex was carried out as described in Section A1. Monomer sulfobetaine methacrylate (SBMA), free initiator EBiB and HMImCl were also dissolved in TFE in identical ratio as described in Section A1, and degassed and combined with the copper catalyst complex. The mixture was stirred for 1 min before being quickly transferred into a flat-bottom reactor containing several pieces of Br-immobilized Ti6Al4V (Ti—Br) substrates under argon atmosphere. Simultaneous solution ATRP and SI-ATRP processes (FIG. 7B) were carried out at both rt and 60° C. An aliquot of the reaction mixture was retrieved for $^1$H NMR and GPC monitoring of the solution pSBMA formation at various time points. Upon termination of the polymerizations by exposure to air, the polymerization solution was precipitated in methanol to obtain free pSBMA while the pSBMA-grafted substrates were washed with TFE using a Soxhlet apparatus for 24 h to remove any non-covalently absorbed free polymers from the substrate and dried under vacuum. Grafting of block polymer brushes pSBMA-b-pTFEMA to the substrate was performed in a similar fashion by feeding hydrophobic TFEMA monomer to pSBMA-grafted (Ti-pSBMA) substrates.

To cleave the surface grafted polymers for characterization of the efficiency of SI-ATRP, the Ti-pSBMA substrates were placed in a 50-mL plastic tube with 30 mL of ionic acid release solution (0.2-M NaCl and 2-M HCl in water), and gently shaken on an orbital shaker at room temperature. The solution was collected after 3 days, neutralized by sodium hydroxide, and dialyzed in a dialysis membrane tubing (Spectra/Por 6, MWCO: 1000) against Milli-Q water for 3 days (with fresh Milli-Q water changes 3 times a day) before it was freeze-dried. GPC analyses of the cleaved surface-grafted pSBMA and the "free" pSBMA formed in the solution showed similar molecular weights and equally low PDI (FIG. 7C, PDI 1.15 vs. 1.18), supporting that the SI-ATRP were carried out with excellent control.

Figure 8:
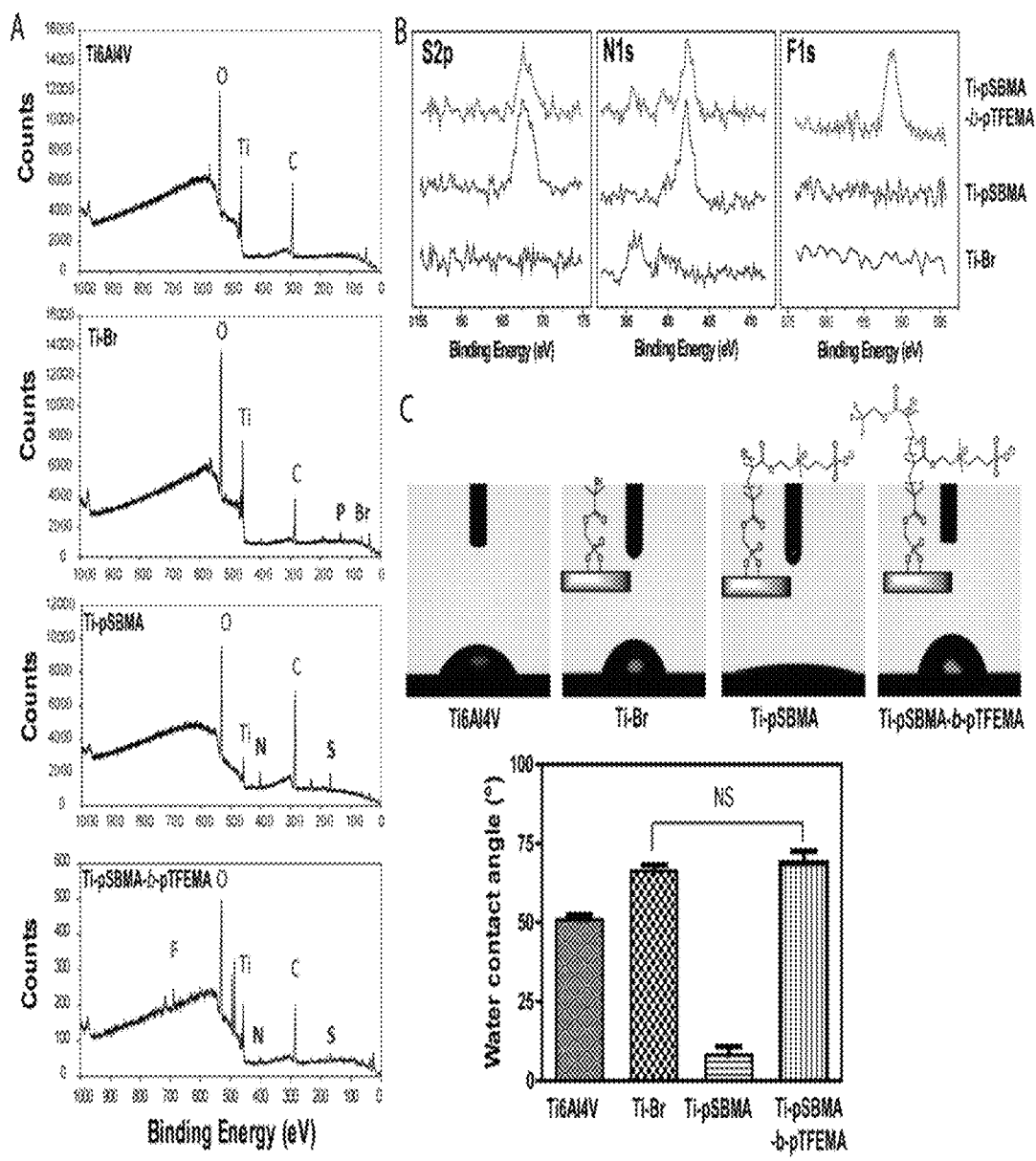
FIG. 8. (A) XPS survey scans, (B) high resolution XPS spectra, and (C) water contact angle measurements (N=3) confirming the covalent attachment of Br-terminated surface initiator (Ti—Br) and subsequent grafting of zwitterionic pSBMA$_{200}$ (DP=200) and block copolymer pSBMA$_{50}$-b-pTFEMA$_{100}$ (DP=50 for pSBMA & DP=100 for pTFEMA) brushes on the Ti6Al4V substrates via SI-ATRP. All pairwise comparisons are significant (p<0.05, one-way ANOVA with Tukey's multiple comparison) unless indicated as NS.

Surface Properties of Ti6Al4V Substrates Surface-Grafted with Zwitterionic pSBMA or Block Copolymer pSBMA-b-pTFEMA Brushes The successful surface attachment of Br-terminated initiators and subsequent grafting of polymer brushes via SI-ATRP were validated by surface chemical composition analysis by X-ray photoelectron spectroscopy (XPS, FIGS. 8A & 8B) and by changes in surface wettability as measured by water contact angles (FIG. 8C).

Characteristic XPS peaks for $Br_{3d}$ and $P_{2p}$ that were absent from the unmodified Ti6Al4V substrate were detected from the Ti—Br substrate (FIG. 8A). Upon grafting of pSBMA, the $S_{2p}$ and $N_{1s}$ signals characteristic for sulfo- betaines were readily detected (FIGS. 8A & 8B) while the $Br_{3d}$ and $P_{2p}$ signals became barely detectable (FIG. 8A), supporting the grafting of pSBMA surface brushes with substantial depth and surface coverage. Upon grafting a second block of pTEFMA, the signal corresponding to $F_{1s}$ appeared while the relative intensity for the $S_{2p}$ and $N_{1s}$ signals decreased (FIGS. 8A & 8B), consistent with a good surface coverage by the fluorinated pTEFMA block.

Water contact angle measurements (N=3) were consistent with the superhydrophilicity of pSBMA-grafted surfaces and the rapid restoration of its hydrophobicity upon grafting of a second hydrophobic pTFEMA block (FIG. 8C). The tight standard deviations observed with the contact angles of multiple specimens support consistent coverage of the surface by the respective grafted polymer brushes.

Reduced Fouling of Ti6Al4V Substrates Upon Surface-Grafting with pSBMA

Figure 9:
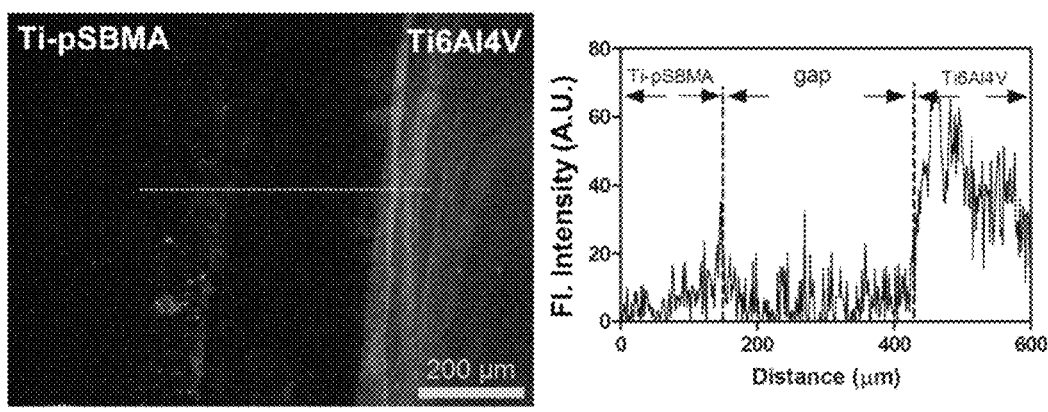
FIG. 9. Florescent microscopy (left) and fluorescent intensity line profiling (right) showing substantially reduced non-specific absorption of fluorescein-conjugated BSA on Ti6Al4V substrate upon surface grafting of pSBMA$_{200}$ (DP=200) on the metallic substrate. Images were taken after overnight incubation with 500-μg/mL BSA-fluorescein conjugate in PBS, followed by rinsing with PBS.

Ti6Al4V specimens with and without surface grafted $pSBMA_{200}$ were each incubated with 1 mL of PBS solution of bovine serum albumin (BSA)-fluorescein conjugate (500 μg/mL) at 37° C. overnight. The substrates were then rinsed with fresh PBS (pH=7.4) three times to remove loosely absorbed BSA. Fluorescent surface-bound proteins were observed by fluorescent microscopy (FIG. 9, left) and the relative fluorescent intensities across the surfaces were quantified by line profiling using ImageJ (FIG. 9, right). The data revealed a significant reduction in non-specific absorption of BSA on the pSBMA-grafted surface, supporting the low-fouling nature of the pSBMA surface polymer brush coating. Since bacterial attachment on a substrate can occur through a layer of adsorbed protein, surfaces that resist adsorption of protein are expected to also resist adsorption of bacteria, although for any given surface, the extent of bacterial resistance does not necessarily correlate linearly with the protein resistance. (Chapman, et al. 2001 *Langmuir* 17, 1225-1233; Ostuni, et al. 2001 *Langmuir* 17, 6336-6343.) Thus, how zwitterionic polymer coated surfaces resist bacterial adhesion will be investigated in parallel to their resistance to protein adsorptions in subsequent studies.

Vancomycin Functionalization

Figure 10:
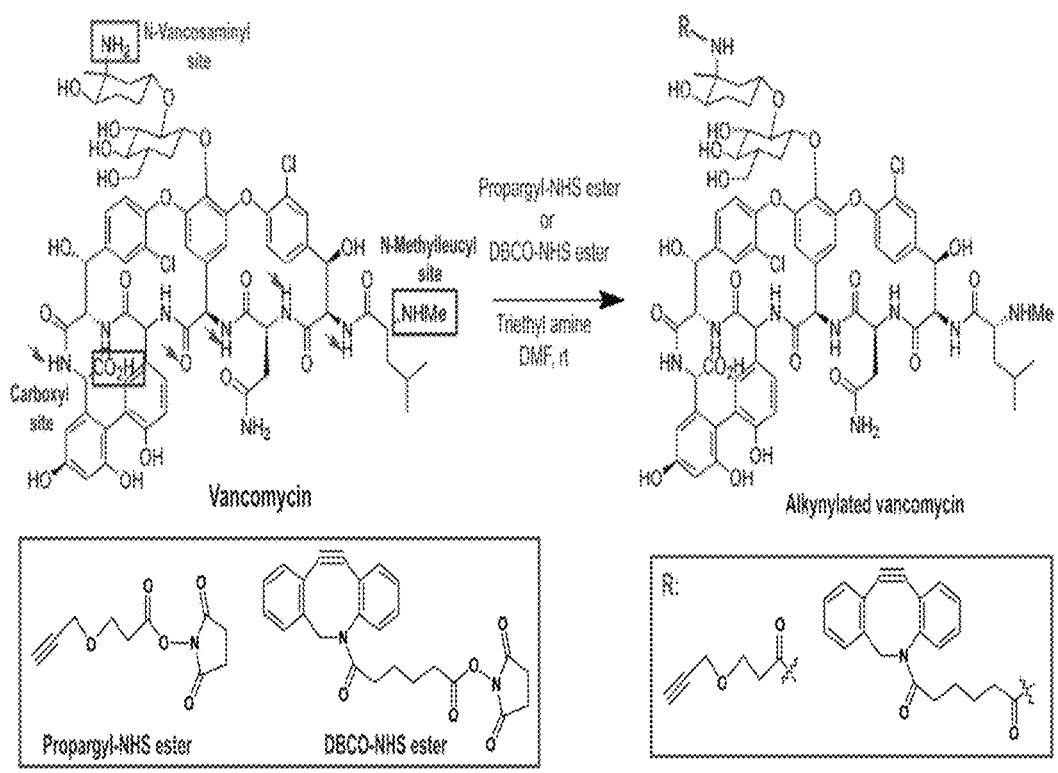
FIG. 10. Potential functionalization sites of vancomycin and proposed representative synthetic strategy for attaching alkynylated vancomycin at the N-vancosaminyl site. Red arrows denote the H-bonding donors/acceptors involved with binding to the L-Lys-D-Ala-D-Ala termini of nascent peptidoglycan. R group can also be attached to N-Methylleucyl and caroboxyl sites. A wide variety of R groups containing C≡C either as end group or within a constrained cyclic structure may be used.

There are three major sites for potential chemical functionalization of vancomycin, the N-vancosaminyl site, the N-methylleucyl site, and the carboxyl site (FIG. 10). For instance, the N-vancosaminyl site is alkynylated by reacting vancomycin at room temperature with 1.1 equivalent of propargyl-NHS ester or dibenzylcyclooctyne-NHS ester (DBCO—NHS ester) (Click Chemistry Tools, Scottsdale, Ariz.) in DMF with 20 equivalent of triethylamine overnight. In addition to azido-alkyne click chemistries, other high-fidelity conjugation chemistries including but limited to thiol-ene coupling, Michael addition of a carbon nucleophile enolate with an electrophilic carbonyl, Diels-Alder reaction, Schiff base formation of a nucleophilic primary or secondary amine with an aldehyde or ketone can also be applied. Standard amidation with activated ester-teminated brushes such as pTFEMA can also be carried out. Among azido-alkyne click chemistries, both Copper (I)-catalyzed and copper-free, strain-promoted chemistries with a wide range of terminal alkynyl groups and strained cyclic alkynes can be employed.

Figure 11:
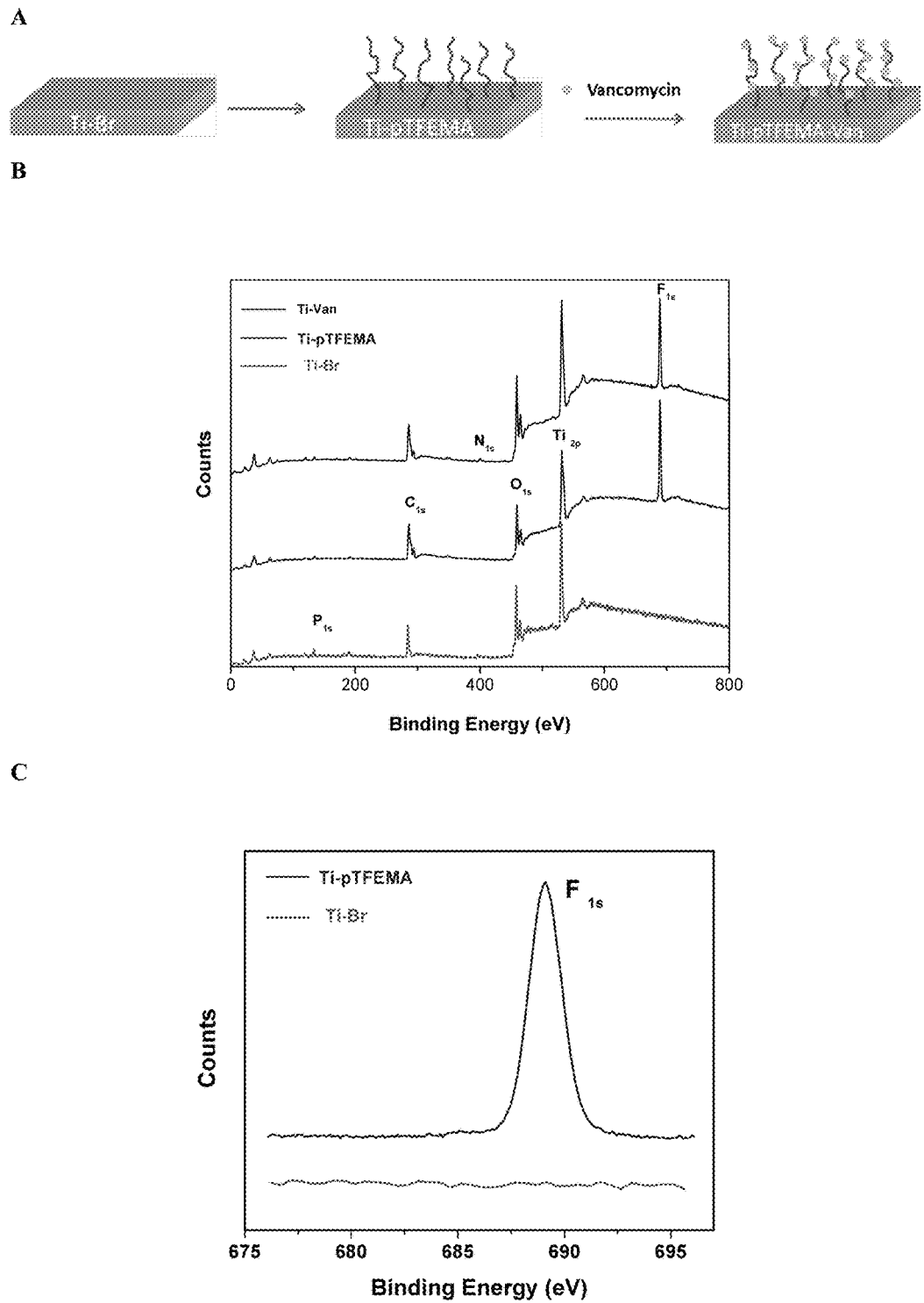
FIG. 11. (A) Conjugation of vancomycin to pTFEMA surface brush-grafted Ti alloy surface, (B) XPS survey scans, (C) high-resolution $F_{1s}$ scans, and (D) high-resolution $N_{1s}$ scans of Ti—Br, pTFEMA-grafted (Ti-pTFEMA) and Vancomycin-functionalized (Ti-Van) Ti alloy surfaces.
Figure 11:
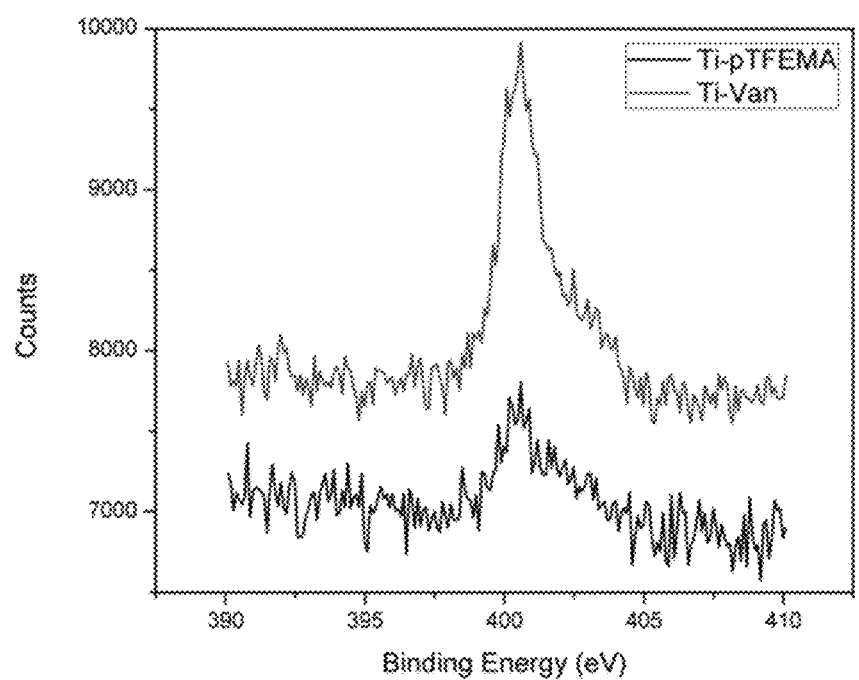

To conjugate vancomycin to pTFEMA brush-grafted Ti alloy, vancomycin (0.15 mmol) was dissolved in TFE (10 mL) under stirring, to which the pTFEMA brush-grafted Ti alloy substrates were then immersed in for 24 h (FIG. 11A). The substrates were retrieved and extracted with fresh TFE for 24 h to remove the physically absorbed vancomycin. The resulting substrates were dried under vacuum and characterized by XPS. The XPS analysis revealed the expected appearance of F1s signal upon grafting pTFEMA to the Ti—Br surface (FIGS. 11B & C), and the increase in $N_{1s}$ signal intensity upon conjugation of vancomycin to the Ti-pTFEMA surface (FIGS. 11B & D).

Figure 12:
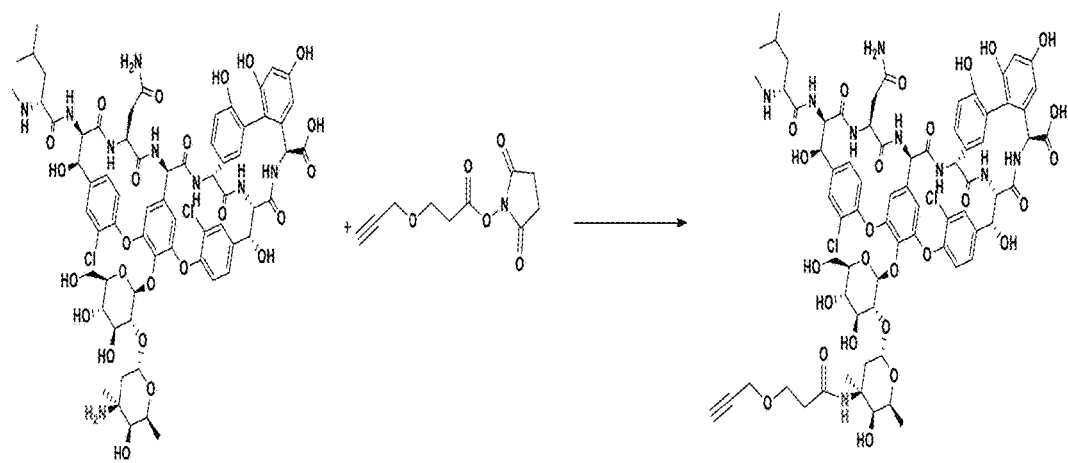
FIG. 12. Synthesis and reverse phase HPLC characterization of alkynylated Vancomycin.
Figure 12:
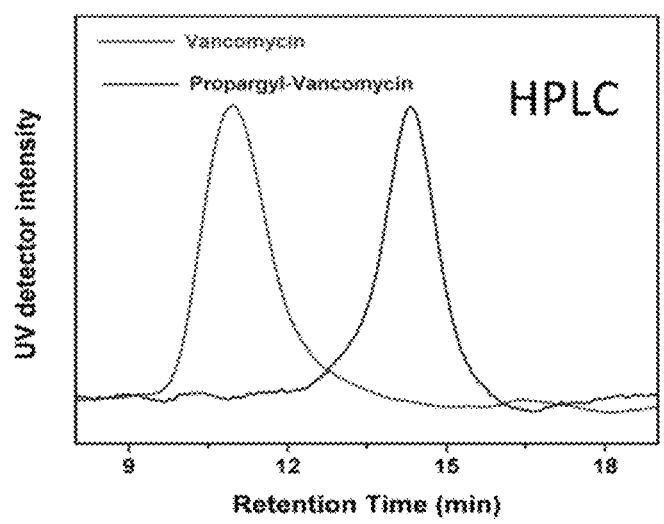

To facilitate alternative conjugation of vancomycin to the substrate via azide-alkyne click chemistry, alkynylated vancomycin was prepared (FIG. 12). To a solution of vancomycin.HCl (0.33 mmol) in dry DMF (6 mL) were added active ester Propargyl-NHS ester (0.36 mmol) and triethylamine (0.66 mmol). After reacting for 24 h at rt under inert argon atmosphere, the solvent was removed under reduced pressure, and the product was precipitated in methanol, collected and lyophilized. The alkynylated product was characterized by reverse phase (Varian Microsorb 100-5, C18 250×4.6 mm analytical column) HPLC, showing expected decrease of polarity (thus longer retention time; Water:CH3CN:TFA=90:10:0.1; flow rate, 1 mL/min). The alkynylated product was purified by preparative HPLC (Varian Dynamax 250×21.4 mm column).

Figure 13:
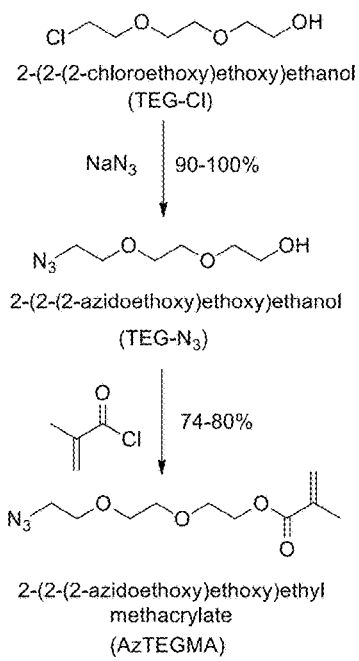
FIG. 13. Synthesis and characterizations of azide-containing monomer. (A) synthetic scheme; (B) & (C)$^1$H and $^{13}$C NMR for TEG-N$_3$; (D) & (E)$^1$H and $^{13}$C NMR for AzTEGMA.
Figure 13:
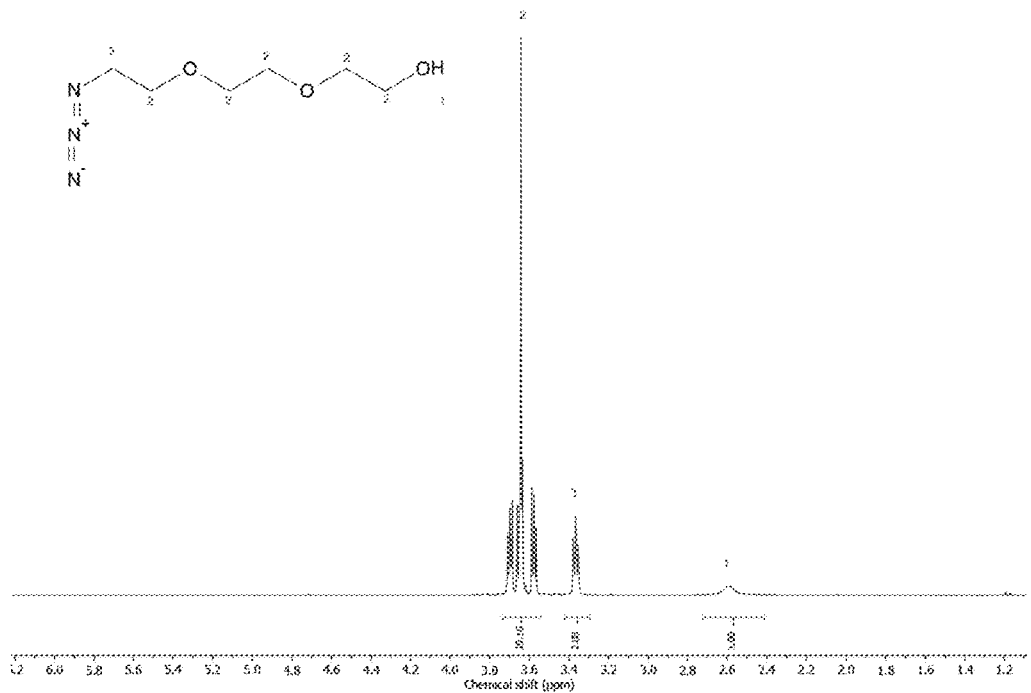
Figure 13:
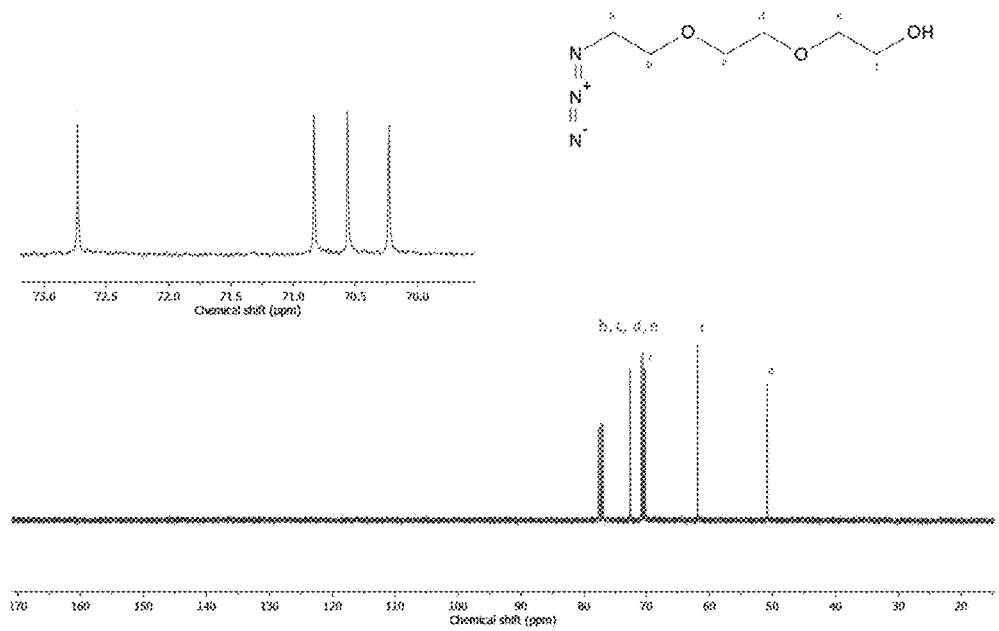
Figure 13:
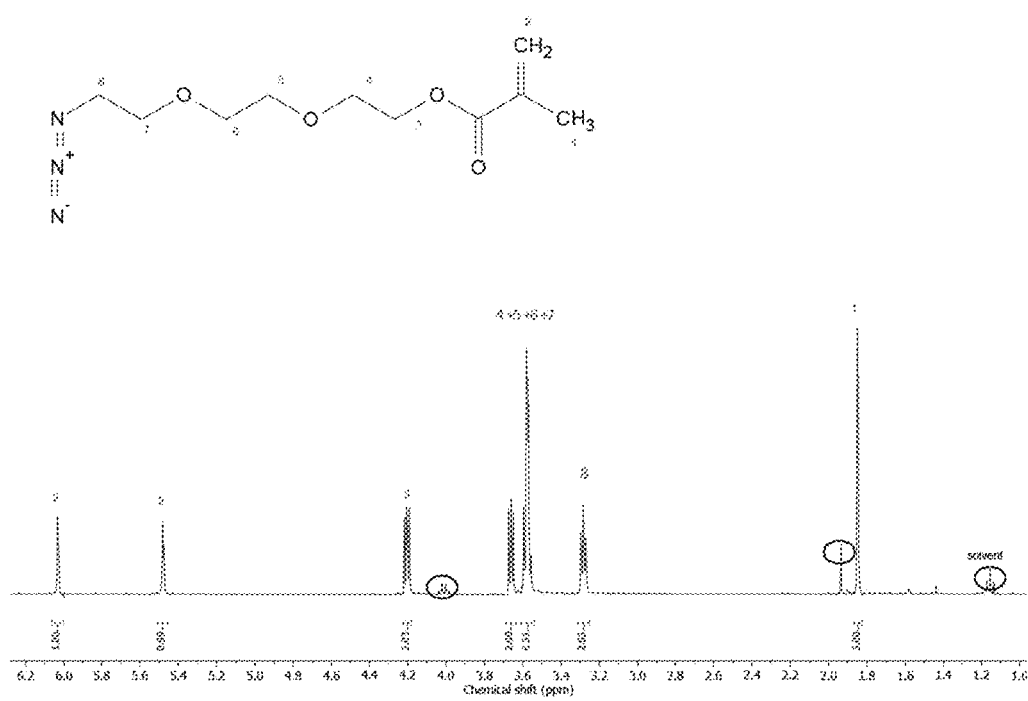
Figure 13:
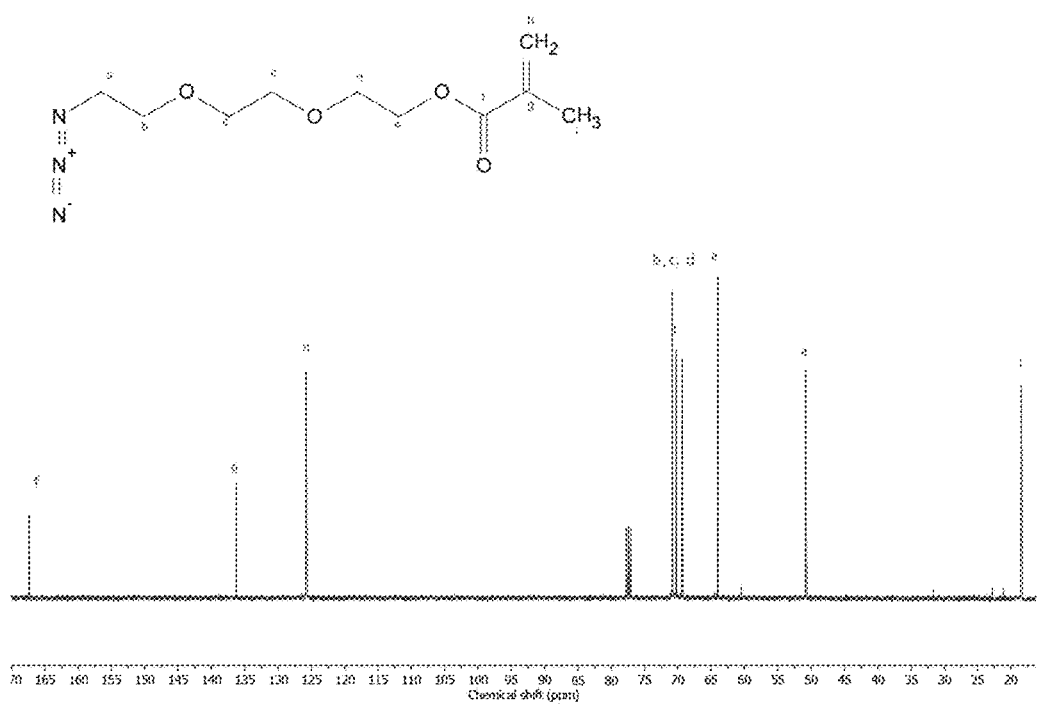

To prepare azide functionalized surface brushes, functional monomer 2-(2-(2-Azidoethoxy)ethoxy)ethanol (AzTEGMA) was synthesized from 2-(2-(2-Chloroethyoxy) ethoxy)-ethanol (TEG-Cl) via intermediate 2-(2-(2-Azidoethoxy)ethoxy)ethanol (TEG-$N_3$) (FIG. 13A). First, sodium azide (0.69 mol) was added to a mixture of water (180 mL) and TEG-Cl (0.36 mol). The mixture was stirred at 75° C. for 48 h and then cooled to rt. Water was evaporated/condensed under reduced pressure over NaOH pellets (0.2 g) to trap any $HN_3$ potentially produced. The mixture was suspended in ether (300 mL). After filtration, the filtrate was concentrated by rotary evaporation to give a colorless liquid of TEG-$N_3$ in 90.5% yield. The TEG-$N_3$ was fully characterized by $^1H$ and $^{13}C$ NMR (FIGS. 13 B & C). To obtain AzTEGMA, TEG-$N_3$ (40 mmol), TEA (45 mmol) and 4-methylphenol (0.05 g) were added to 80 mL of benzene and allowed to cool to 0° C. Methacryloyl chloride (48 mmol) in 20 mL of benzene was added drop-wise into the mixture. The reaction was slowly warmed to rt and stirred overnight. The resulting mixture was filtered, and the filtrate was concentrated and subjected to silica column chromatography purification to give final product in 75.6% yield. The AzTEGMA product was fully characterized by $^1H$ and $^{13}C$ NMR (FIGS. 13 D & E).

Figure 14:
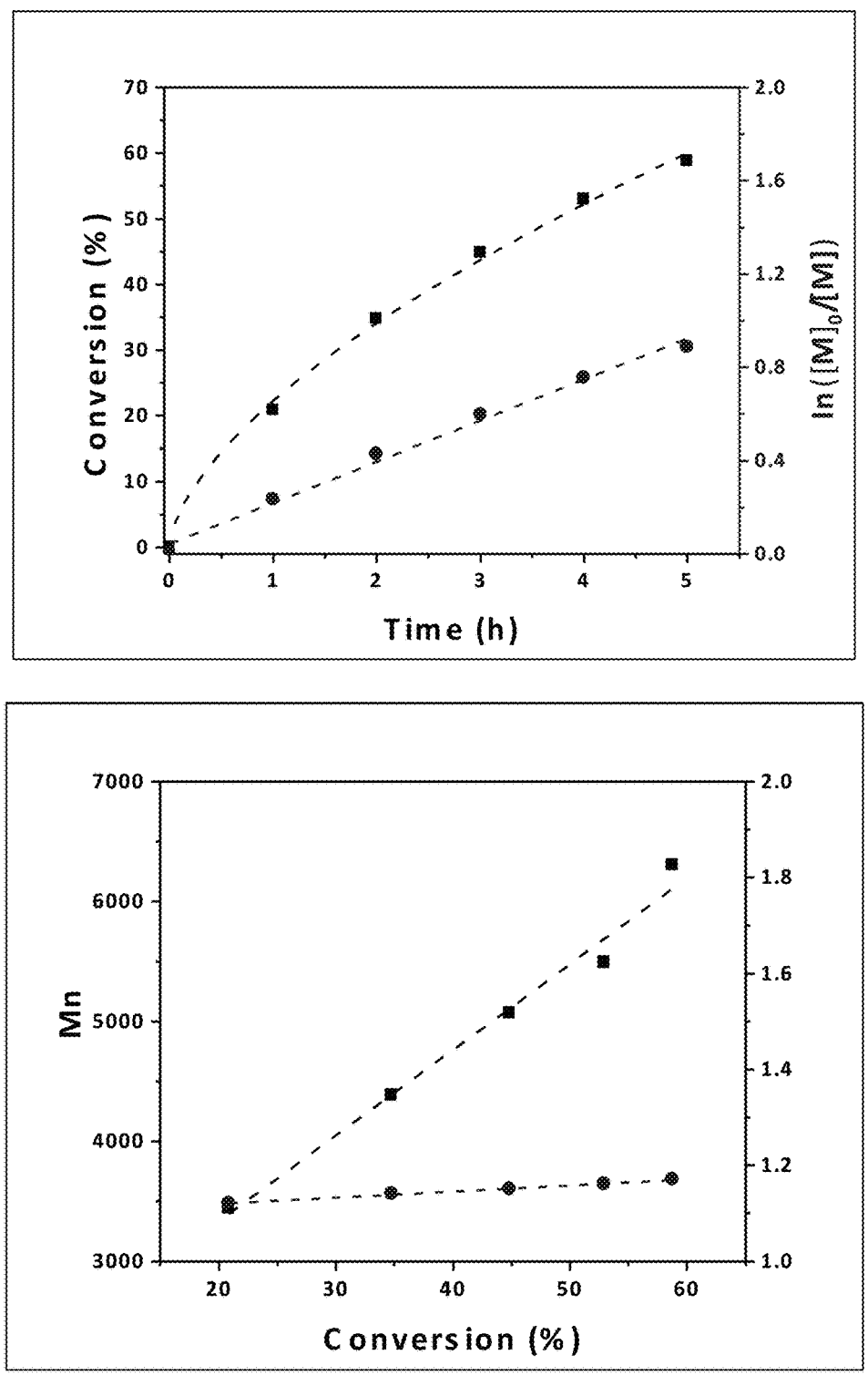
FIG. 14. GPC characterization of the kinetics, conversion, and polydispersity index (PDI) of solution polymerization of AzTEGMA by ATRP.
Figure 14:
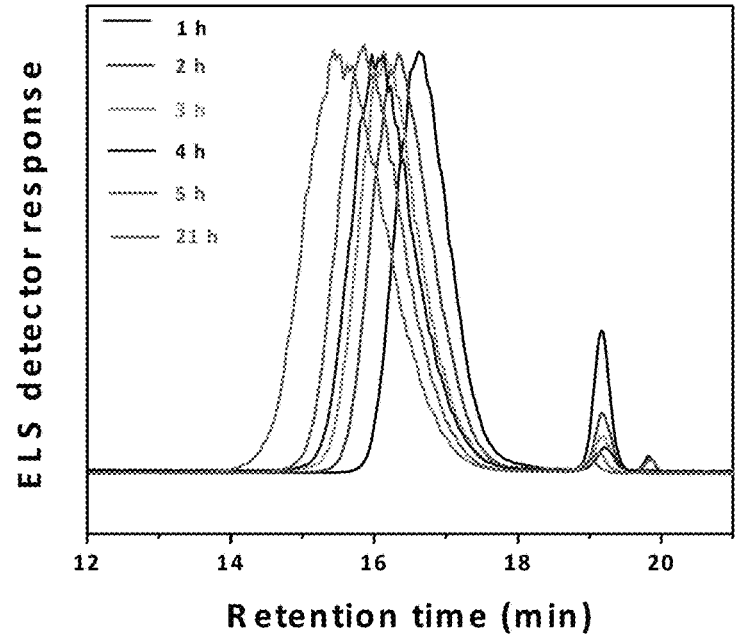
Figure 14:
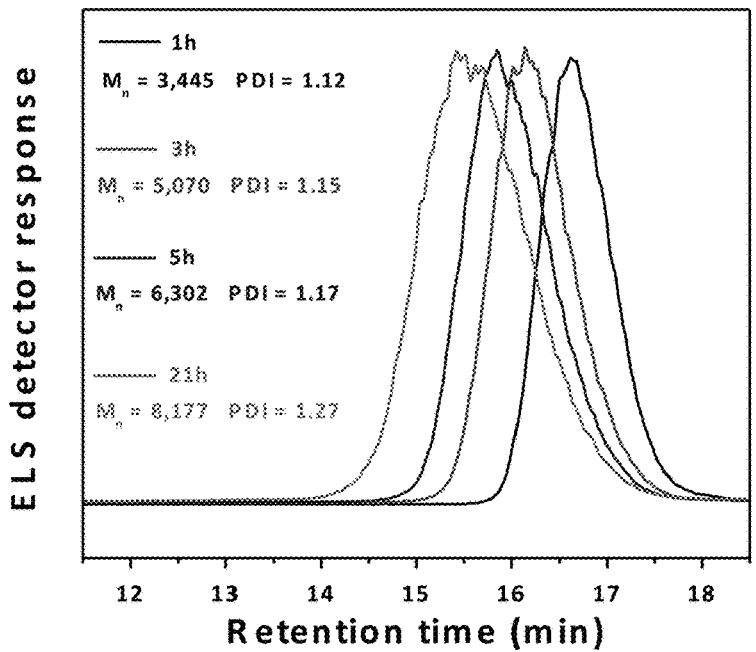

ATRP of AzTEGMA was carried out. Briefly, BPY (0.2 mmol) and TFE (1 mL) were charged into a dry Schlenk flask. After three "freeze-pump-thaw" cycles to move oxygen, the flask was back filled with argon followed by the addition of CuBr (0.1 mmol) under argon protection. The mixture was stirred until a uniform dark brown catalyst complex was formed. AzTEGMA (10 mmol), EBiB (0.1 mmol) and TFE under (1 mL) were charged into another Schlenk flask, degassed by three "freeze-pump-thaw" cycles, before the uniform catalyst complex was injected by syringe. The ATRP proceeded at rt, and aliquots of the reaction mixture were retrieved for $^1H$ NMR and GPC monitoring over time. The GPC characterization of the ATRP kinetics, conversion, and polydispersity (PDI) are shown in FIG. 14.

It should be noted that click chemistry that may be utilized herein encompasses a wide range of reactions that have broad utilities. Click reactions are characterized by selectivity, facile experimental set-up, applicability in aqueous and aerobic systems, tolerance to a variety of functional groups, quantitative yields, and minimal synthetic work-up. (Golas, et al. 2010 *Chem. Soc. Rev.* 39, 1338.) In recent years, a number of bioorthogonal reactions have been developed, exemplified by click chemistry. The ability to rationally incorporate reactive tags onto a biomolecular target and subsequently achieve high selectivity in tag derivatization within a complex biological sample has revolutionized the toolbox that is available for addressing fundamental issues. (Best 2009 *Biochemistry* 48 (28), pp. 6571-6584.) Well-known reactions include the hetero-Diels-Alder reaction, the thiol-ene coupling, the Staudinger ligation, native chemical ligation, the amidation reaction between thio acids and sulfonyl azides (sulfo-click), and copper(I)-catalyzed alkyne-azide cycloaddition (CuAAC) and copper-free, strain-promoted. alkyne-azide cycloaddition (SPAAC) (See, e.g., Dijk, et al. 2009 *Bioconjugate Chem.* 20 (11), pp. 2001-2016; Hoyle, et al. 2010 *Chem. Soc. Rev.* 39, 1355; Jewett, et al. 2010 *Chem. Soc. Rev.* 39, 1272; Sumerlin, et al. 2010 *Macromolecules* 43 (1), pp. 1-13; Hang, et al. 2001 *Accounts of Chemical Research* 34, 727-73; and Kiick, et al. 2002 *Proc. Natl. Acad. Sci. USA* 99, 2007-2010; Xu, et al. 2011 *Macromolecules,* 44, 2660-2667; and Xu, et al. 2011 *Chem-Asian J.* 6 (10), 2730-2737.)

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A co-polymer comprising repeating units having structures of:

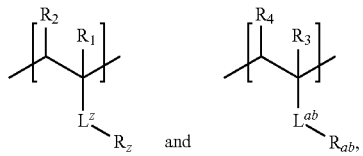

and wherein
- $R_1$, $R_3$ each is independently a hydrogen, alkyl, alkyloxy;
- $R_2$, $R_4$ each is independently a hydrogen, $(C_1$-$C_{15})$ alkyl, $(C_1$-$C_{15})$ alkyloxy;
- $L^z$ is a linking group;
- $L^{ab}$ is a linking group;
- $R_z$ is a pendant group comprising a zwitterionic group; and
- $R_{ab}$ is a pendant group comprising an antibacterial moiety, wherein the antibacterial moiety is vancomycin or a derivative thereof.

2. The co-polymer of claim 1, wherein the co-polymer comprises the structure:

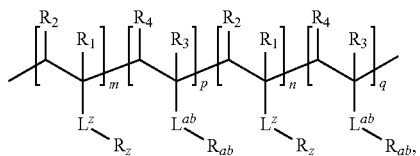

wherein each of m, n, p, and q is an integer selected from about 0 to about 500.

3. The co-polymer of claim 1, wherein the zwitterionic group is selected from phosphorylcholine, sulfobetaine, and carboxybetaine.

4. The co-polymer of claim 2, comprising repeating units of structures:

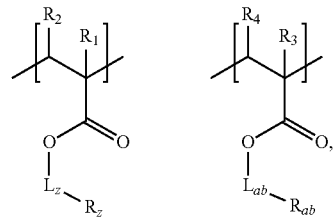

wherein
- $L_z$ is a linking group; and
- $L_{ab}$ is a linking group.

5. The co-polymer of claim 4, wherein the co-polymer comprises the structure:

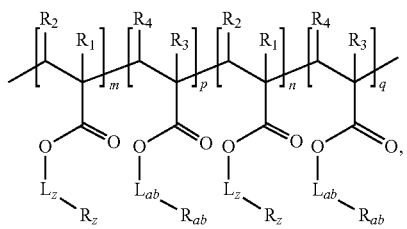

wherein each of m, n, p, and q is an integer selected from about 0 to about 500.

6. The co-polymer of claim 5, wherein each of $R_1$, $R_3$, $R_2$, and $R_4$ is hydrogen.

7. The co-polymer of claim 5, wherein at least one of $R_1$, $R_3$, $R_2$, and $R_4$ is not hydrogen.

8. The co-polymer of claim 6, wherein each of $L_z$ and $L_{ab}$ is independently —$(CH_2)_i$—, wherein i is an integer from about 1 to about 20.

* * * * *